(12) United States Patent
Wang et al.

(10) Patent No.: US 10,900,051 B2
(45) Date of Patent: Jan. 26, 2021

(54) GENE FOR IMPROVING PLANT DISEASE RESISTANCE AND USE THEREOF

(71) Applicant: NANJING AGRICULTURAL UNIVERSITY, Jiangsu (CN)

(72) Inventors: Yuanchao Wang, Nanjing (CN); Yan Wang, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 4 days.

(21) Appl. No.: 16/180,170

(22) Filed: Nov. 5, 2018

(65) Prior Publication Data
US 2019/0136257 A1  May 9, 2019

(30) Foreign Application Priority Data
Nov. 3, 2017 (CN) .......................... 2017 1 1067417

(51) Int. Cl.
| | | |
|---|---|---|
| *A01H 1/00* | (2006.01) | |
| *A01H 5/00* | (2018.01) | |
| *C12N 15/00* | (2006.01) | |
| *C12N 15/82* | (2006.01) | |
| *C07K 14/415* | (2006.01) | |

(52) U.S. Cl.
CPC ........... *C12N 15/8282* (2013.01); *A01H 1/00* (2013.01); *A01H 5/00* (2013.01); *C07K 14/415* (2013.01); *C12N 15/00* (2013.01)

(58) Field of Classification Search
None
See application file for complete search history.

(56) References Cited

U.S. PATENT DOCUMENTS

2017/0058292 A1* 3/2017 Jehle .................. C12N 15/8281

OTHER PUBLICATIONS

William Fry. "Phytophthora Infestans: The Plant (and R Gene) Destroyer". Molecular Plant Pathology, 2008, vol. 9, No. 3, pp. 385-402.
Kurt H. Lamour et al. "The Oomycete Broad-Host-Range Pathogen Phytophthora Capsici". Molecular Plant Pathology, 2012, vol. 13, No. 4, pp. 329-337.
Vivianne G.A.A. Vleeshouwers et al. "Understanding and Exploiting Late Blight Resistance in the Age of Effectors". Annual Review of Phytopathology, 2011, vol. 49, pp. 25.1-25.25.
Sophien Kamoun et al. "Resistance to Oomycetes: A General Role for the Hypersensitive Response?" Trends in Plant Science, May 1999, vol. 4, No. 5, pp. 196-200.
Sylvain Raffaele et al. "Genome Evolution in Filamentous Plant Pathogens: Why Bigger Can Be Better". Nature Reviews Microbiology, May 2012, vol. 10, 15 pages.
Pieter M.J.A. Van Poppel et al. "The Phytophthora Infestans Avirulence Gene Avr4 Encodes an RXLR-dEER Effector". Molecular Plant-Microbe Interactions, Nov. 2008, vol. 21, No. 11, pp. 1460-1470 and 10 pages of supplemental material.
Thomas Boller et al. "A Renaissance of Elicitors: Perception of Microbe-Associated Molecular Patterns and Danger Signals by Pattern-Recognition Receptors". Annual Review of Plant Biology, vol. 60, pp. 379-406. 2009.
Tingting Liu et al. "Chitin-Induced Dimerization Activates a Plant Immune Receptor". Science Magazine, Jun. 1, 2012, vol. 336, No. 6085, pp. 1160-1164.
Yadong Sun et al. "Structural Basis for FLG22-Induced Activation of the *Arabidopsis* FLS2-BAK1 Immune Complex". Science Magazine, Nov. 1, 2013, vol. 342, No. 6158, pp. 624-628.
Kana Naito et al. "Amino Acid Sequence of Bacterial Microbe-Associated Molecular Pattern FLG22 Is Required for Virulence". Molecular Plant-Microbe Interactions, 2008, vol. 21, No. 9, pp. 1165-1174.
Zhenchuan Ma et al. "A Phytophthora Sojae Glycoside Hydrolase 12 Protein Is a Major Virulence Factor During Soybean Infection and Is Recognized as a Pamp". The Plant Cell, Jul. 2015, vol. 27, with supplemental data, 33 pages.
Yiyu Dong et al. "A Ligation-Independent Cloning Tobacco Rattle Virus Vector for High-Throughput Virus-Induced Gene Silencing Identifies Roles for NbMADS4-1 and -2 in Floral Development". Plant Physiology, Dec. 2007, vol. 145, pp. 1161-1170.
Kenneth J. Livak et al. "Analysis of Relative Gene Expression Data Using Real-Time Quantitative PCR and the 2-ΔΔct Method". Methods, 2001, vol. 25, pp. 402-408.

* cited by examiner

*Primary Examiner* — Phuong T Bui
(74) *Attorney, Agent, or Firm* — Oliff PLC

(57) ABSTRACT

The ReXEG1 gene for improving plant disease resistance has a nucleotide sequence as shown in SEQ ID NO. 1, and encodes a product having an amino acid sequence as shown in SEQ ID NO. 3. It has a key role in resistance of tobacco to *Phytophthora* pathogens. Overexpression of this gene significantly promotes the resistance of tobacco to various *Phytophthora* species, and is a desirable gene for enhancing the plant disease resistance. The gene is allowed to express in tobacco by genetic transformation to improve resistance to various pathogens to tobacco, thereby improving the disease resistance of crops in field.

13 Claims, 2 Drawing Sheets
Specification includes a Sequence Listing.

GENE FOR IMPROVING PLANT DISEASE RESISTANCE AND USE THEREOF

BACKGROUND

Technical Field

The present invention relates to the field of plant molecular biology and plant genetic engineering, and in particular to a gene for improving plant disease resistance and use thereof.

Background

*Phytophthora* species are an important class of plant pathogens, and often cause serious damage of crops. Among them, the potato late blight caused by *Phytophthora infestans* was responsible for the Great Famine in Ireland and other European countries in the 19th century, resulting in the death of nearly one million people and the migration of millions of people to other countries. At present, late blight is still an important problem restricting the potato and tomato production, leading to over billions of dollars annual economic loss all over the world [1]. Moreover, *Phytophthora capsici*[2] and *Phytophthora parasitica* are also important *Phytophthora* pathogens that pose great threat to the crop production. Both species infect a wide range of hosts and can cause damage to a variety of Solanaceous plants such as tomatoes, peppers and tobacco. Under suitable environmental conditions, *Phytophthora* pathogens can spread rapidly on infected plants and cause mass death of plants in a short period of time. The diseases caused by *Phytophthora* pathogens are notoriously difficult to control because the pathogens are fast evolving and are capable to resist chemical pesticides. In addition, extensive application of chemical pesticides in the field often causes serious environmental problems. Therefore, improving the durable disease resistance of crop varieties is of great significance for the effective control of *Phytophthora* diseases Studies on *Phytophthora* resistant genes in plants are mainly focused on a class of genes encoding receptor protein containing nucleotide binding sites (NBS) and leucine-rich repeats (LRR)[3]. The NBS-LRR disease-resistant proteins encoded by this class of genes act inside of the plant cells, and can recognize the cytoplasmic effectors secreted by *Phytophthora* to activate the defense response in plants, thereby inhibiting the infection of *Phytophthora*[4]. However, the recognition of the *Phytophthora* effectors by the NBS-LRR disease-resistant proteins in plants follows the "gene-to-gene" model, that is, the NBS-LRR disease-resistant proteins can only recognize specific effector molecules secreted by *Phytophthora*. Once the effector molecules secreted by *Phytophthora* undergo mutations, the NBS-LRR disease-resistant protein will lose its resistant function to *Phytophthora*[5]. The effectors secreted by different *Phytophthora* isolates are highly diverse[6], and thus the NBS-LRR proteins confer only isolate-specific resistance to *Phytophthora*. As the composition of *Phytophthora* isolates changes constantly in the field, most of the resistance genes cloned in plants encoding NBS-LRR proteins have lost their resistance to *Phytophthora*[3]. Therefore, identification of genes with broad-spectrum and long-lasting disease resistance to *Phytophthora* pathogens are effective ways to improve the crop resistance.

In plants, there is a large number of cell membrane-localized receptors, which have a structure including an extracellular domain, a transmembrane domain and an intracellular domain. This class of proteins is involved in the recognition of conserved molecular patterns released by pathogens or plants during infection, and activates basal defense responses in plants, including: cell death, reactive oxygen burst, expression of immune-related genes, and synthesis of secondary metabolites[7]. Several genes encoding cell membrane immunoreceptors have been cloned in plants, such as FLS2 and CERK1[8-9]. The two pattern recognizing receptors activate the disease-resistance response in plants by recognizing the bacterial flagellin and the fungal cell wall component chitin, respectively. Flagellin and chitin are important components in bacteria and fungi, respectively, and play an important role in the pathogenicity of pathogens[10]. Given the importance of such components, it is difficult for pathogens to escape the recognition by plant cell membrane receptors by modifying such conserved molecules. Therefore, the plant cell membrane immunoreceptors are often confer broad-spectrum and durable disease resistance.

XEG1 is a newly identified molecule pattern that is highly conserved in pathogens including fungi, oomycetes and bacteria. XEG1 can be recognized by plants to elicit immune responses in plants[11]. However, how cell membrane receptors recognize such molecular pattern and confer plant resistance is still unknown at present.

REFERENCES

[1] Fry, W 2008. *Phytophthora infestans*: the plant (and R gene) destroyer. Molecular Plant Pathology, 9(3): 385-402.

[2] Lamour, K. H., Stam R., Jupe, J., and Huitema E. 2012. The oomycete broad-host-range pathogen *Phytophthora capsici*. Molecular Plant Pathology, 13(4): 329-337.

[3] Vleeshouwers, V. G. A. A., Raffaele, S., Vossen, J. H., Champouret, N., Oliva, R., Segretin, M. E., Rietman, H., Cano, L. M., Lokossou, A., Kessel, G., Pel, M. A., and Kamoun, S. 2011. Understanding and exploiting late blight resistance in the age of effectors. Annual Review of Phytopathology, 49: 507-531.

[4] Kamoun, S., Huitema, E., and Vleeshouwers, V. G. A. A. 1999. Resistance to oomycetes: a general role for the hypersensitive response? Trends in Plant Science, 4(5): 196-200.

[5] Raffaele, S., and Kamoun, S. 2012. Genome evolution in filamentous plant pathogens: Why bigger can be better? Nature Reviews Microbiology, 10: 417-430.

[6] van Poppel, P. M. J. A., Guo, J., Van De Vondervoort, P. J. I., Jung, M. W., Birch, P. R., Whisson, S. C., and Govers, F. 2008. The *Phytophthora infestans* avirulence gene Avr4 encodes an RXLR-dEER effector. Molecular Plant-Microbe Interactions, 21(11): 1460-70.

[7] Boller, T., and Felix, G. 2009. A renaissance of elicitors: Perception of microbe-associated molecular patterns and danger signals by pattern-recognition receptors. Annual Review of Plant Biology, 60: 379-406.

[8] Liu, T., Liu, Z., Song, C., Hu, Y., Han, Z., She, J., Fan, F., Wang, J., Jin, C., Chang, J., Zhou, J. M., and Chai, J. 2012. Chitin-induced dimerization activates a plant immune receptor. Science, 336(6085):1160-1164.

[9] Sun, Y, Li, L., Macho, A. P., Han, Z., Hu, Z., Zipfel, C., Zhou, J. M., and Chai, J. 2013. Structural basis for flg22-induced activation of the *Arabidopsis* FLS2-BAK1 immune complex. Science, 342(6158): 624-628.

[10] Naito K., Taguchi F., Suzuki T., Inagaki Y, Toyoda K., Shiraishi T., and Ichinose Y. 2008. Amino acid sequence of bacterial microbe-associated molecular pattern flg22 is required for virulence. Molecular Plant-Microbe Interactions, 21(9): 1165-1174.

[11] Ma Z., Song T., Zhu L., Ye W., Wang W, Shao Y, Dong S., Zhang Z., Dou. D., Zheng X., Tyler, B. M., and Wang Y. 2015. A *Phytophthora sojae* glycoside hydrolase 12 protein is a major virulence factor during soybean infection and is recognized as a PAMP. Plant Cell, 27: 2057-2072.

SUMMARY

The first objective of the present invention is to provide a ReXEG1 gene.

The second objective of the present invention is to provide a recombinant expression vector comprising the ReXEG1 gene.

The third objective of the present invention is to provide use of the ReXEG1 gene.

The present invention is described in detail as below.

The present invention provides a ReXEG1 gene, derived from tobacco and having a nucleotide sequence as shown in SEQ ID NO. 1.

The present invention further provides a fragment silencing the ReXEG1 gene having a nucleotide sequence as shown in SEQ ID NO. 2.

The present invention also provides a protein encoded by the ReXEG1 gene or a protein having an amino acid sequence of not less than 50% similarity, including an amino acid sequence of not less than 80% similarity, to the protein encoded by the ReXEG1 gene. The protein encoded by the ReXEG1 gene provided in the present invention has an amino acid sequence as shown in SEQ ID NO. 3, and the protein having an amino acid sequence of not less than 50% similarity to the protein encoded by the ReXEG1 gene includes those having an amino acid sequence as shown in SEQ ID NO. 4 or SEQ ID NO. 5.

In embodiments, the present invention provides nucleic acid sequences that have at least 50% sequence identity, at least 80% sequence identity, at least 85% sequence identity, at least 90% sequence identity, at least 95% sequence identity, at least 98% sequence identity, and at least 99% sequence identity to SEQ ID NO: 1. The present invention also provides nucleic acid sequences that have at least 50% sequence identity, at least 80% sequence identity, at least 85% sequence identity, at least 90% sequence identity, at least 95% sequence identity, at least 98% sequence identity, and at least 99% sequence identity to any of SEQ ID NOS: 2, 6, 7, 8, 9, 10, 11, 12, or 13.

In further embodiments, the present invention provides amino acid sequences that have at least 50% sequence identity, at least 80% sequence identity, at least 85% sequence identity, at least 90% sequence identity, at least 95% sequence identity, at least 98% sequence identity, and at least 99% sequence identity to SEQ ID NO: 3. The present invention also provides amino acid sequences that have at least 50% sequence identity, at least 80% sequence identity, at least 85% sequence identity, at least 90% sequence identity, at least 95% sequence identity, at least 98% sequence identity, and at least 99% sequence identity to SEQ ID NO: 4 or SEQ ID NO: 5.

"Sequence identity" is determined by techniques known in the art, including the Basic Local Alignment Search Tool (BLAST) computer program and underlying algorithm(s). BLAST may be accessed online through the National Center for Biotechnology Information (NCBI) website.

Using the amino acid sequence encoded by the gene of the present invention, a signal peptide sequence can be designed and artificially added to facilitate the expression in plants.

Using the amino acid sequence encoded by the gene of the present invention, a codon-optimized nucleic acid sequence can be designed and artificially synthesized to facilitate the expression in plants.

The present invention further provides a recombinant expression vector comprising the ReXEG1 gene.

The expression vector is preferably a plant plasmid for transformation, and may be the expression vector pBin::eGFP, pCambia or pTF101.1.

Preferably, the recombinant expression vector is the vector pBin::ReXEG1-eGFP obtained by inserting the ReXEG1 gene into a binary vector pBin::eGFP containing a C-terminal eGFP at the cleavage site KpnI.

The present invention also provides a recombinant silencing vector comprising a fragment silencing the ReXEG1 gene.

The silencing vector is preferably a plant plasmid for transformation, which may be the silencing vector pTRV2.

Preferably, the recombinant silencing vector is the vector pTRV2::ReXEG1 obtained by inserting a specific fragment of ReXEG1 into the viral silencing vector pTRV2 at the cleavage site PstI.

A transformant is provided, which is obtained by introducing the recombinant expression vector into a host cell, where the host cell is preferably an *Escherichia coli* cell or an *Agrobacterium* cell.

The present invention also provides use of the ReXEG1 gene, a protein encoded, or a recombinant expression vector or a transformant thereof to improve immune resistance or disease resistance in plants.

The present invention also provides use of the ReXEG1 gene, a protein encoded, or a recombinant expression vector or a transformant thereof in the improvement of immune resistance to plant pathogens or in the improvement of resistance to diseases caused by plant pathogens.

Further, the pathogens mentioned in the present invention are pathogens capable of secreting XEG1 protein, and may be oomycetes or fungi such as *Phytophthora* species, *Verticillium dahliae, Botrytis cinerea*, and other pathogens causing plant diseases.

The present invention also provides use of the ReXEG1 gene, a protein encoded, or a recombinant expression vector or a transformant thereof in plant breeding.

The present invention also provides use of the ReXEG1 gene derived from tobacco, a protein encoded, or a recombinant expression vector or a transformant thereof in the production of a plant variety with notable disease resistance and/or increased yield after introduction into a plant, preferably tobacco, tomato, potato or soybean.

In this study, the analysis of cell membrane receptors in tobacco reveals that the immunoreceptor ReXEG1 is involved in the recognition of XEG1, and plays a critical role in the immune responses induced by this pattern molecule in different pathogens. More importantly, this gene confers resistance to different *Phytophthora* pathogens. The lesions caused by inoculating *Phytophthora capsici* and *Phytophthora parasitica* in tobacco over-expressing the ReXEG1 gene are significantly reduced when compared with the control plants. The ReXEG1 gene plays a very important role in the disease resistance of tobacco. In addition, tobacco is an important representative of economic crops and Solanaceae. The study of ReXEG1 in tobacco can give incentive to study the cell membrane receptors in many other plants such as tomato and potato. In addition, XEG1 is conserved in various fungal and bacterial pathogens, and ReXEG1 is also required for the recognition of the XEG1 protein secreted by the fungal pathogen, *Verticillium dahliae*, indicating that ReXEG1 may also confer resistance to fungal pathogens. These studies are able to elucidate the plant resistance to *Phytophthora* and various pathogens, and provide excellent disease-resistant gene resources for disease-resistant genetic engineering breeding.

Beneficial Effects of the Present Invention

The protein encoded by the ReXEG1 gene of the present invention activates plant innate immunity by recognizing a conserved pattern molecule secreted by oomycete and fungal pathogen, thereby enhancing the plant disease resistance. Overexpression in plants does not affect the plant growth traits, but significantly increases the plant resistance to *Phytophthora*. The present invention is applicable to breeding of crops with respect to improvement of disease resistance, and is expected to improve the disease resistance of plants, thereby achieving the purpose of increasing production and reducing the use of pesticides.

DETAILED DESCRIPTION

Figure 1:
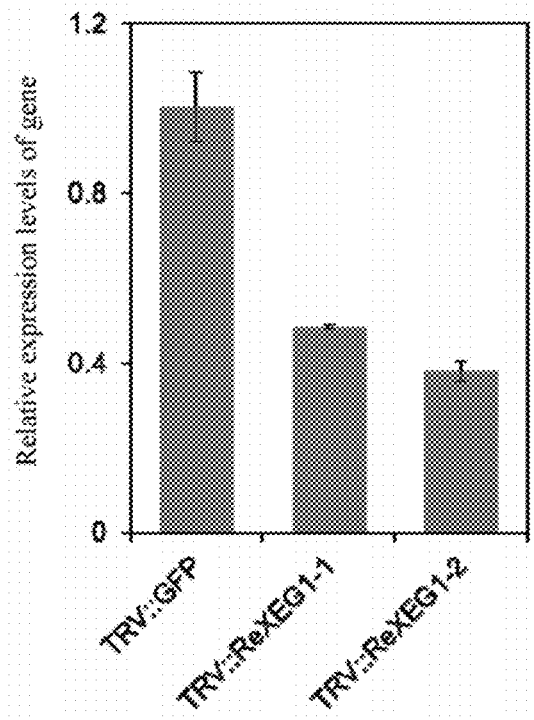
FIG. 1 shows the detection of ReXEG1 expression in the TRV::ReXEG1 silencing tobacco. Real-time quantitative PCR is used to detect the expression of ReXEG1 gene in the silencing tobacco, in which TRV::GFP is used as the control plant, and −1 and −2 are different ReXEG1-silencing plants.

The following examples are provided for a better understanding of the present invention; however, the present invention is not limited thereto. The methods given in examples below are all conventional methods, unless it is otherwise stated. Test materials used in the following examples are commercially available, unless otherwise specified. The primers involved in the examples of the present invention were synthesized by Nanjing GenScript Biotech Corp.

Example 1. Cloning and Sequencing of ReXEG1 Gene

The seeds of tobacco (*Nicotiana benthamiana*) were directly sown in pots filled with nutrient soil, and cultivated in a greenhouse (at 21-23° C. and 14 h light/10 h dark), and six-week-old plants were used for RNA extraction.

Extraction of total RNA: Tobacco leaves were used as raw materials. Total RNA was extracted using a RNA extraction kit available from Omega following the instructions. The RNA content and quality were measured by a spectrophotometer.

Production of the first strand by reverse transcription: 0.7 µg of RNA was used as a template, cDNA was synthesized following the instructions for use of Takara's PrimeScript reverse transcriptase kit, and the volume was adjusted to 20 µL. An appropriate amount of product obtained after reverse transcription was taken for subsequent gene cloning by PCR.

The first strand of cDNA was used as a template for RT-PCR, and PCR was performed following a conventional process to amplify a fragment of the ReXEG1 gene or the full length gene:

Primer sequences for PCR amplification:

Upstream primer:
SEQ ID NO. 6
(5'-
TTACGAACGATAGCCGGTACCATGGGCAAAAGGGAATATCCAAG -3')

Downstream primer:
SEQ ID NO. 7
(5'-
GCTCACCATCCCGGGGGTACCAGCCCTTAACTTTCTCTTCAGTC -3')

The 50 µL reaction system contained 10 µL of 5× buffer, 4 µL of 2.5 mM dNTPs, 0.5 µL of Takara PrimerSTAR Taq enzyme, 1 µL of template cDNA, and water q.s. to 50 µL. PCR amplification procedure comprised 40 cycles of pre-denaturation at 98° C. for 2 min, denaturation at 98° C. for 30 s, annealing at 58° C. for 10 s, and extension at 72° C. for 3.5 min, and final extension at 72° C. for 10 min. After separation by agarose gel electrophoresis, ethidium bromide (EB) staining, and photographing, the results were recorded, and the PCR product of ReXEG1 was recovered by gel extraction. The bands resulting from electrophoresis were recovered using Agarose Gel DNA Purification Kit (Ta-KaRa). The PCR product of ReXEG1 recovered by extraction was ligated to the pBin::eGFP vector cleaved by KpnI following the instructions for use of the ClonExpress II One Step Cloning Kit (Vazyme) to obtain the pBin::ReXEG1-eGFP plasmid. The plasmid was transformed into *E. coli* competent cell GM109. The cells were plated on an LB plate (containing 50 µg/mL Kan), and cultured at 37° C. for 16 hrs. Verification by colony PCR was performed. Three clones were picked up, and the plasmid was extracted using a plasmid extraction kit (Takara), and shipped to Nanjing GenScript Biotech Corp. for sequencing. The sequence is as shown in SEQ ID NO. 1. The plasmid sequenced to be correct was electroporated into *Agrobacterium* GV3101. The cells were plated on an LB plate (containing 50 µg/mL Kan and 50 ug/mL Rif). After incubation at 30° C. for 48 h, the colonies were verified by PCR, and the correct colony was picked up for the subsequent experiments.

Example 2. Construction of Silencing Vector TRV2::ReXEG1

Total RNA was extracted from tobacco and cDNA was synthesized by reverse transcription. The primers were designed based on the sequence of ReXEG1, and used to amplify the fragments for construction of ReXEG1 gene silencing vector.

Upstream primer:
                                    SEQ ID NO. 8
5'-CGACAAGACCCTGCAGGTTTCAAGAGATAACTAAAC-3'

Downstream primer:
                                    SEQ ID NO. 9
5'-GAGAAGAGCCCTGCAGAAGAATTGGCTATTTCAGC-3'

A 103 bp-long fragment of the sequence of SEQ ID NO. 1 was amplified by PCR. PCR amplification procedure comprised 40 cycles of pre-denaturation at 98° C. for 2 min, denaturation at 98° C. for 30 s, annealing at 58° C. for 10 s, and extension at 72° C. for 0.5 min, and final extension at 72° C. for 10 min. The PCR product was separated by 1% agarose gel electrophoresis, followed by ethidium bromide (EB) staining, and photographing. The PCR product was recovered using Agarose Gel DNA Purification Kit (Ta-KaRa). The PCR product recovered by extraction was ligated to the pTRV2 vector cleaved by PstI following the instructions for use of the ClonExpress II One Step Cloning Kit (Vazyme), to obtain the pTRV2::ReXEG1 plasmid. The plasmid was transformed into *E. coli* competent cell GM109. The cells were plated on an LB plate (containing 50 μg/mL Kan), and cultured at 37° C. for 16 hrs. Verification by colony PCR was performed. Three clones were picked up, and the TRV2::ReXEG1 plasmid was extracted using a plasmid extraction kit (Takara). The sequence is as shown in SEQ ID NO. 2. The plasmid with correct sequence was electroporated into *Agrobacterium* GV3101. The cells were plated on an LB plate (containing 50 μg/mL Kan and 50 ug/mL Rif). After incubation at 30° C. for 48 h, the colonies were verified by PCR, and the correct colony was picked up for the subsequent experiments.

Example 3. Virus-Induced ReXEG1 Gene Silencing in Tobacco

The procedures were listed as follows.
1) *Agrobacterium* Culture
Single colonies of *Agrobacterium* GV3101 transfected with the pTRV2::ReXEG1 vector (ReXEG1 gene silencing vector), control *Agrobacterium* GV3101 containing pTRV2::GFP vector, and *Agrobacterium* GV3101 containing viral pTRV1 were picked up from the plates respectively, inoculated separately into 2 mL LB liquid medium (containing 50 μg/mL Kan and 50 μg/mL Rif), and incubated overnight on a shaker at a constant temperature of 30° C. and 200 rpm until OD600 was 2.0. The *Agrobacterium* GV3101 suspension cultured overnight was centrifuged at 3000 g for 5 min to collect the cells. The cells were suspended in a buffer (comprising 10 mM 2-[N-morpholino] ethanesulfonic acid, 10 mM $MgCl_2$, and 200 μM acetosyringone pH 5.6), and then centrifuged to collect the cells. The cells were repeatedly washed 3 times, and then diluted in a buffer. pTRV1 mixed with *Agrobacterium* transfected with pTRV2::ReXEG1 and pTRV2::GFP respectively in a 1:1 ration to a final concentration of 1.0
2) Gene Silencing in Tobacco
The prepared *Agrobacterium* suspension was injected into leaves of the 2-week old tobacco seedlings with a syringe. The treated tobacco seedlings were cultivated for four weeks in a climate chamber (at 21-23° C. and 14 h light/10 h dark) and then tested for the gene silencing levels.

REFERENCE

Dong, Y., Burch-Smith, T. M., Liu, Y., Mamillapalli, P., Dinesh-Kumar, S. P. 2007. A ligation-independent cloning TRV vector for high-throughput virus induced gene. Plant Physiology, 145, 1161-1170.
3) Detecting of ReXEG1 Silencing Efficiency
Total RNA was extracted from tobacco leaves after four weeks of silencing. Tobacco leaves were used as raw materials. Total RNA was extracted using a RNA extraction kit from Omega following the manufacturer's instructions. The RNA content and quality were measured by a spectrophotometer.
Production of first strand cDNA was performed by reverse transcription: 0.7 μg of RNA was used as template, cDNA was synthesized following the instructions for use of Takara's PrimeScript reverse transcriptase kit, and the volume was adjusted to 20 μL. The product obtained after reverse transcription was 10-fold diluted with water for detecting the gene silencing efficiency by real-time quantitative PCR.
Real-time quantitative PCR:

Forward primer for quantification:
                                    SEQ ID NO. 10
5'-GCTCCTTAACAAATTTAGAGGCG-3'

Reverse primer for quantification:
                                    SEQ ID NO. 11
5'-TGATTGGTGAAATGCTGCCATAG-3'

The PCR reaction system contained 5 μL of cDNA, 10 μL of SYBR Premix Ex Taq II (Tli RNase H Plus), each 0.4 μL of the forward primer and the reverse primer, 0.4 μL of ROX Reference Dye II, and 13.8 μL of water. Reaction procedure: I): 30 s at 95° C.; II): 40 cycles of 5 s at 95° C. and 34 s at 60° C. Procedure for analyzing of melting curve: 15 s at 95° C., 1 min at 60° C., and 15 s at 95° C. The data was analyzed by $2^{-\Delta\Delta C_T}$ method. The detection results are shown in FIG. 1.

REFERENCE

Livak, K. J., and Schmittgen, T. D. (2001). Analysis of relative gene expression data using real-time quantitative PCR and the $2^{-\Delta\Delta C_T}$ method. Methods 25, 402-408.

Example 4. Transient Expression of XEG1 Protein Secreted by Different Pathogens on Silencing Tobacco 1) *Agrobacterium* Culture
Single colonies of *Agrobacterium* GV3101 transfected with XEG1 gene carrying vectors secreted by *Phytophthora sojae*, *Phytophthora parasitica*, *Phytophthora infestans*, and *Verticillium dahliae* were picked up from the plates respectively, inoculated separately into 2 mL LB liquid medium (containing 50 μg/mL Kan and 50 μg/mL Rif), and incubated overnight on a shaker at a constant temperature of 30° C. and 200 rpm until OD600 was 2.0. The *Agrobacterium* GV3101 suspension cultured overnight was centrifuged at 3000 g for 5 min to collect the cells. The cells were suspended in a buffer (comprising 10 mM 2-[N-morpholino] ethanesulfonic acid, 10 mM $MgCl_2$, and 200 μM acetosyringone pH 5.6), and then centrifuged to collect the cells. The cells were repeatedly washed 3 times, and then dilute the bacterial suspensions to a final concentration of 0.2, respectively.
2) *Agrobacterium* suspensions containing XEG1 homologous gene vectors was injected to 6-week-old tobacco leaves, and the infiltrated tobacco plants were maintained in a climate chamber (at 21-23° C. and 14 h light/10 h dark) after injection. Three days after injection, the cells were photographed and the cell death status was recorded.

Figure 2:
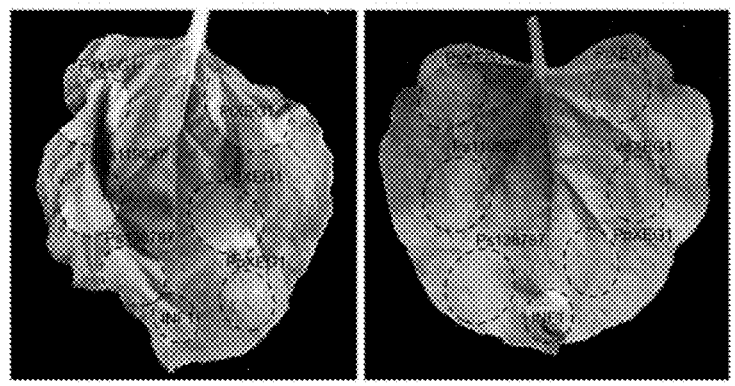
FIG. 2 shows the cell death induced by expression of XEG1 protein secreted by various *Phytophthora* pathogens and *Verticillium dahliae* on the ReXEG1 silencing plants. Ps: *Phytophthora sojae Kaufman Gerdman*, Pi: *Phytophthora infestans* (Mont.) *de Bary*, Pp: *Phytophthora parasitica*, and Vd: *Verticillium dahliae*.

Expression of the 6 homologous XEG1 proteins secreted by different *Phytophthora* and *Verticillium dahliae* induces cell death in the pTRV2::GFP treated plants, but failed to induce any cell death in the tobacco leaves with the silencing of the receptor ReXEG1, as shown in FIG. 2. These results confirm that ReXEG1 has broad-spectrum recognition for XEG1 proteins.

Example 5. Inoculation of *Phytophthora parasitica* on Silencing Tobacco

Figure 3:
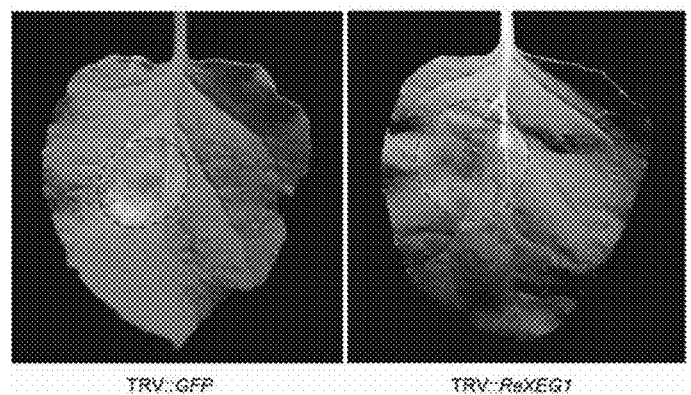
FIG. 3 shows disease symptoms on the TRV::GFP and TRV::ReXEG1 treated tobacco after inoculation with *Phytophthora parasitica*.

Silencing tobacco plants were placed in a plastic box and the leaves were inoculated with fresh *Phytophthora parasitica* plugs with a diameter of 5 mm, and maintained under high humidity in the covered plastic box. The inoculated plants were maintained in the dark for 24 h and then kept in a growth chamber at 21-23° C. and 14 h light/10 h dark. Disease symptoms were photographed three days after inoculation. Compared with the plants treated with the control TRV::GFP, the leaves with silent ReXEG1 show significantly increased disease spots after inoculation with *Phytophthora parasitica* (FIG. 3). These results confirm that ReXEG1 is required for the resistance of tobacco to *Phytophthora*.

Example 6. Expression of ReXEG1 Gene in Tobacco

1) *Agrobacterium* Culture

Single colonies of *Agrobacterium* GV3101 transfected with pBin::ReXEG1-eGFP vector (binary ReXEG1 gene expression vector, with the sequence shown in SEQ ID NO. 12, pBin::eGFP vector (having a sequence partially as shown in SEQ ID NO. 13), and the silencing suppressor P19 were inoculated separately into 2 mL LB liquid medium (containing 50 μg/mL Kan and 50 μg/mL Rif), and incubated overnight on a shaker at a constant temperature of 30° C. and 200 rpm until OD600 was 2.0. The *Agrobacterium* GV3101 suspension cultured overnight was centrifuged at 3000 g for 5 min to collect the cells. The cells were re-suspended in a buffer (comprising 10 mM 2-[N-morpholino] ethanesulfonic acid, 10 mM $MgCl_2$, and 200 μM acetosyringone pH 5.6), and then centrifuged to collect the cells. The cells were repeatedly washed 3 times, and then diluted in the buffer. P19 was 1:1 mixed with *Agrobacterium* transfected with pBin::ReXEG1-eGFP or pBin::eGFP, to give a final concentration of 0.6 for each.

2) Expression of ReXEG1 in Tobacco

The *Agrobacterium* suspension was injected into tobacco leaves by a syringe. The infiltrated tobacco plants were cultivated in a growth chamber (at 21-23° C. and 14 h light/10 h dark) after injection.

3) Detection of the Amount of ReXEG1 Protein

Figure 4:
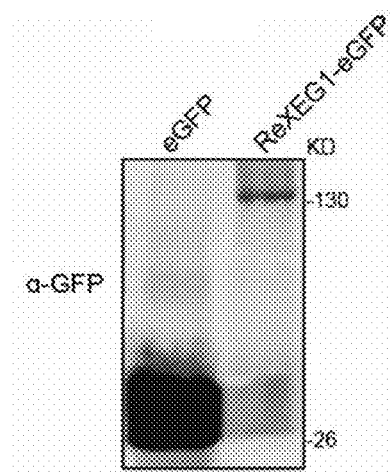
FIG. 4 shows detection of protein expression in pBin:: eGFP and pBin::ReXEG1-eGFP transgenic tobacco. The expression levels of control eGFP and ReXEG1-eGFP are detected by Western blot with anti-GFP antibody.

Tobacco leaves were collected two days after infiltration to determine the accumulation of protein. The collected tobacco leaves were quickly frozen in liquid nitrogen, ground, and added to a protein extracting buffer (containing 150 mM NaCl, 50 mM Tris-HCl pH 7.5, 10 mM ethylenediaminetetraacetic acid, 1.0% (v/v) NP-40, 1 mM phenylmethylsulfonyl Fluoride, and 1.0% (v/v) protease inhibitor cocktail). The samples were mixed thoroughly, and kept on ice for 30 min. 80 μL of the supernatant was collected by centrifugation at 18000 g, mixed with 20 μL of 5× protein loading buffer and boiled for 10 min. 20 μL of the sample was separated by SDS-PAGE gel at 120 V for 1.5 h. After the reaction, the protein sample was transferred to a PVDF membrane, and the membrane was blocked using 5% PBST milk. After incubating for 2 hours in the 1:5000 diluted GFP primary antibody (Abmart), the membrane was washed three times with PBST for 5 min, followed by addition of 1:10000 diluted anti-mouse secondary antibody (LI-COR, irdye 800, 926-32210) and incubation for 30 minutes. The membrane was washed three times with PBST for 5 min before photographed (FIG. 4).

4) Overexpression of ReXEG1 Significantly Enhances the Resistance of Tobacco to *Phytophthora capsici* and *Phytophthora parasitica*

Figure 5:
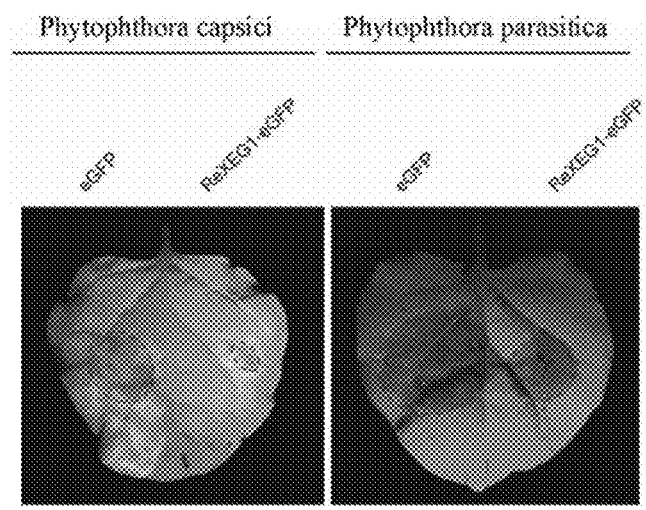
FIG. 5 shows disease symptoms on pBin::eGFP and pBin::ReXEG1-eGFP transgenic tobacco. A: disease symptoms two days after inoculation with *Phytophthora capsici*. B: disease symptoms three days after inoculation with *Phytophthora parasitica*.

Two days after infiltration, the leaves were inoculated with plugs of *Phytophthora capsici* and *Phytophthora parasitica*. Disease symptoms were observed at 2 and 3 days after inoculation (FIG. 5), and the results were photographed. Compared with the negative control, the tobacco leaves overexpressing ReXEG1 shows significant reduced disease symptom after inoculation with *Phytophthora*, and these results confirm that overexpression of ReXEG1 significantly enhances the resistance of tobacco to various *Phytophthora*.

In summary, these results demonstrated that the ReXEG1 gene has a key role in resistance to *Phytophthora* pathogens. Overexpression of this gene significantly promotes the resistance of tobacco to different *Phytophthora* pathogens, and is a desirable gene for enhancing the plant disease resistance. The gene is allowed to express in tobacco by genetic transformation to impart resistance to various pathogenic bacteria to tobacco, thereby improving the disease resistance of crops in the field.

What is claimed is:

1. A recombinant expression vector comprising:
   an ReXEG1 gene comprising SEQ ID NO:1 operably linked to
   a heterologous nucleic acid sequence.

2. The recombinant expression vector according to claim 1, wherein the ReXEG1 gene encodes a protein comprising SEQ ID NO: 3.

3. The recombinant expression vector according to claim 1, wherein the vector is obtained by inserting the ReXEG1 gene into a binary vector.

4. A transformant obtained by introducing the recombinant expression vector according to claim 1 into a host cell.

5. The transformant according to claim 4, wherein the host cell is an *Escherichia coli* cell or an *Agrobacterium* cell.

6. A transgenic plant obtained by transformation, whereby transformation comprises introducing an *Agrobacterium* host cell comprising the recombinant expression vector according to claim 1 into a plant and transferring the ReXEG1 gene into cells of the plant for expression of the protein encoded by the ReXEG1 gene.

7. The transgenic plant according to claim 6, wherein the plant is a tobacco, tomato, potato, or soybean plant.

8. The transgenic plant according to claim 6, wherein the transgenic plant has improved immune resistance to *Phytophthora* sp. or *Verticillium* sp. due to expression of the protein encoded by the ReXEG1 gene as compared to an otherwise identical plant that does not express the protein encoded by the ReXEG1 gene.

9. The transgenic plant according to claim 6, wherein the plant has improved resistance to disease caused by *Phytophthora* sp. or *Verticillium* sp. due to expression of the protein encoded by the ReXEG1 gene as compared to an otherwise identical plant that does not express the protein encoded by the ReXEG1 gene.

10. A method of obtaining a transgenic plant by transformation, whereby transformation comprises:
    introducing an *Agrobacterium* host cell comprising the recombinant expression vector according to claim 1 into a plant; and
    transferring the ReXEG1 gene into cells of the plant such that the plant expresses the protein encoded by the ReXEG1 gene.

11. A method for growing a transgenic plant, comprising:
    growing the transgenic plant according to claim 6 in presence of a plant pathogen selected from the group consisting of *Phytophthora* sp. and *Verticillium* sp.; and
    expressing the protein encoded by the ReXEG1 gene during growth of the transgenic plant.

12. The method according to claim 11, wherein the transgenic plant has improved immune resistance to the plant pathogen due to expression of the protein encoded by the ReXEG1 gene as compared to an otherwise identical plant that does not express the protein encoded by the ReXEG1 gene.

13. The method according to claim 11, wherein the plant has improved resistance to disease caused by the plant pathogen due to expression of the protein encoded by the ReXEG1 gene as compared to an otherwise identical plant that does not express the protein encoded by the ReXEG1 gene.

* * * * *

SEQUENCE LISTING

```
<160> NUMBER OF SEQ ID NOS: 13

<210> SEQ ID NO 1
<211> LENGTH: 3072
<212> TYPE: DNA
<213> ORGANISM: Nicotiana benthamiana

<400> SEQUENCE: 1
atgggcaaaa gggaatatcc aagttcagct catttccttg ttactttgtc tttactgctc      60
ctacaagcag cttttggatt gactctgtgt atagaaaagg agagagatgc ccttcttgaa     120
ttcaaaagag gtcttagtga taattttggt caattatcaa catggggtga tgaagaagat     180
aaaaaagaat gttgcaaatg gaaaggtatt gaatgtaaca aaacaaccgg tcatgtaatt     240
```

```
gttcttgatc ttcataatgc ctttacttgt tctgctagtg cttgttttgc tccaagattg    300
acaggtaaac ttagtccttc tttacttgag ttggagtatt tgaatttctt ggaccttagt    360
gtgaatgaat ttgaaagaag tgaaatacca agattcatat gctcctttaa gagactagag    420
tatttgaacc tctcatcttc ctttttttct ggtttaattc ctacacagtt caagaatcta    480
acttcattga ggattcttga tcttggatat aataatctta tagtaaagga ccttacatgg    540 cttttctcatc tctcttctct agagttattg agtctaggtg gtagtgactt ccaagtaaag    600
aattggtttc aagagataac taaacttcct ttattgaaag aacttgactt gagtctttgt    660
ggactctcta attagttcc atctccagct gaaatagcca attcttcttt gatctctctt    720
tctgttcttc atttatgttg taatgagttt tcttcttcag ctaaatatag ctggttgttc    780
aattttagca caagcttaac tagtatagac ctctcaaata atcagctaga cggtcaaatt    840
gatgatcgat ttgggaactt gatgtatctt gaacatctta atcttgcaaa tgagcttaat    900
cttaaaggtg ggattccaag ttcttttggc aatttgacac gtttacgtta tctggacatg    960
tctaacactc gaacatacca atggcttcct gagttgtttg tcagattatc aggcagtagg   1020
aaaacacttg aggttttggg gttgaacgac aactcaatgt ttggttcatt ggttgatgtc   1080
acaagatttt cagccttaaa gagattatac ctgcagaaaa atgtgctgaa tggttttttc   1140
atggaaagat ttgacaagt ttcgagcctt gagtatctag acttatctga taaccaaatg   1200
agagggccat taccagattt agcattgttt ccatcattga gagagttgca tctcggatct   1260
aatcacttca atgggaggat accacaaggt attggaaaac tttcacagct taaaattttg   1320
gacgtctcgt ccataggct ggaaggatta ccagaaagta tggggcagct gtcgaacctg   1380
gaaagttttg atgcctctta caatgtcctg aagggtacaa tcactgagtc ccacctttca   1440
aatctctcca gttagtgga tttgactta tcgttcaact cgttggcttt gaagacgagc   1500
atcgattggc ttcctccttt tcagcttcaa gttataaacc ttccatcttg caatttggga   1560
ccttctttcc ccaagtggct tcaaagtcaa acaattata ctgttcttga tatctctctt   1620
gcaaatattt cagacgcgct tccaagttgg ttctcaggtt tacctcccga tataaagatt   1680
ttgaatctct ccaacaacca aatcagtgga agagtatctg acttaataga gaatgcatat   1740
gattacatgg taatagattt aagctctaac aacttttcag gacctttgcc attagttcct   1800
accaatgtgc aaatatttta cctgcacaaa aatcagtttt tcggatccat ctcttccatt   1860
tgtaaaagta caacaggagc cacttccctt gacctatcac acaaccaatt ctcaggagag   1920
cttcctgatt gttggatgaa tgcgactaat ctagctgttc ttaatctagc ctataacaat   1980
ttctctggaa aacttccaca gtcattaggc tccttaacaa atttagaggc gttatacatg   2040
cgccagaaca gttttagtgg aatgttgcct tctttatcac aatgtcagtc tttgcaaatc   2100
ttggatcttg gaggaaataa gctgacagga agaatcccag catggatagg gactgaccta   2160
ctcaacttgc gcattctaag cctgcggttc aacaaattct atggcagcat ttcaccaatc   2220
atttgtcagc ttcagtttct tcagatactg gacctttcag caaatggttt agctggcaaa   2280
attccacaat gcttcaataa ttttaccctta ctgcatcaag aaaatggttt gggcgagcca   2340
atggaatttc tagttcaagg tttctatggc aaatatcctc gacattactc gtacctaggc   2400
aatttattgg ttcaatggaa aaaccaggag gctgagtaca agaatccttt aacatatctg   2460
aagactattg atcttttcaag taacaagttg gttggaggta tccctaaaga aatggctgaa   2520
atgagaggat tgaaatcttt gaacctttca cgaaatgatc tgaatggaag tatcattaaa   2580
ggaataggtc aaatgaagat gttggagtca cttgacctgt caagaaacca gctttctggt   2640
```

```
atgattccta aagaccttgc taacttgact tttattggtg tgttggactt gtcaaacaac    2700
cacttatcag ggagaattcc atcaagcact caactccaaa cttttgagag atcatcctac    2760
agtggtaacg ctcaactctg cggtcctcct cttcaagaat gtcccggata tgctcccct     2820 agcccacgta tcgatcataa cagcaacatg aatcctcaag aacttgacgt tgatgatgat    2880
tttccatctc tggagtttta tatatcgatg gtgctaggtt tctttgttgc attctgggga    2940
atcttgggct ctttaattgt caatcattct tggaggaatg cctacttcat attcttaatg    3000
gacacgaaga attggctcgc tatgatatca agagtctgtt gttcaagact gaagagaaag    3060
ttaagggctt ga                                                       3072
```

<210> SEQ ID NO 2
<211> LENGTH: 103
<212> TYPE: DNA
<213> ORGANISM: Artificial Sequence
<220> FEATURE:
<223> OTHER INFORMATION: gene silencing fragment

<400> SEQUENCE: 2

```
ggtttcaaga gataactaaa cttcctttat tgaaagaact tgacttgagt ctttgtggac     60
tctctaaatt agttccatct ccagctgaaa tagccaattc ttc                      103
```

<210> SEQ ID NO 3
<211> LENGTH: 1023
<212> TYPE: PRT
<213> ORGANISM: Nicotiana benthamiana

<400> SEQUENCE: 3

```
Met Gly Lys Arg Glu Tyr Pro Ser Ser Ala His Phe Leu Val Thr Leu
1               5                   10                  15

Ser Leu Leu Leu Leu Gln Ala Ala Phe Gly Leu Thr Leu Cys Ile Glu
            20                  25                  30

Lys Glu Arg Asp Ala Leu Leu Glu Phe Lys Arg Gly Leu Ser Asp Asn
        35                  40                  45

Phe Gly Gln Leu Ser Thr Trp Gly Asp Glu Asp Lys Lys Glu Cys
    50                  55                  60

Cys Lys Trp Lys Gly Ile Glu Cys Asn Lys Thr Thr Gly His Val Ile
65                  70                  75                  80

Val Leu Asp Leu His Asn Ala Phe Thr Cys Ser Ala Ser Ala Cys Phe
                85                  90                  95

Ala Pro Arg Leu Thr Gly Lys Leu Ser Pro Ser Leu Leu Glu Leu Glu
            100                 105                 110

Tyr Leu Asn Phe Leu Asp Leu Ser Val Asn Glu Phe Glu Arg Ser Glu
        115                 120                 125

Ile Pro Arg Phe Ile Cys Ser Phe Lys Arg Leu Glu Tyr Leu Asn Leu
    130                 135                 140

Ser Ser Ser Phe Phe Ser Gly Leu Ile Pro Thr Gln Phe Lys Asn Leu
145                 150                 155                 160

Thr Ser Leu Arg Ile Leu Asp Leu Gly Tyr Asn Asn Leu Ile Val Lys
                165                 170                 175

Asp Leu Thr Trp Leu Ser His Leu Ser Ser Leu Glu Leu Leu Ser Leu
            180                 185                 190

Gly Gly Ser Asp Phe Gln Val Lys Asn Trp Phe Gln Glu Ile Thr Lys
        195                 200                 205

Leu Pro Leu Leu Lys Glu Leu Asp Leu Ser Leu Cys Gly Leu Ser Lys
```

```
                210                 215                 220
Leu Val Pro Ser Pro Ala Glu Ile Ala Asn Ser Ser Leu Ile Ser Leu
225                 230                 235                 240

Ser Val Leu His Leu Cys Cys Asn Glu Phe Ser Ser Ala Lys Tyr
                245                 250                 255

Ser Trp Leu Phe Asn Phe Ser Thr Ser Leu Thr Ser Ile Asp Leu Ser
                260                 265                 270

Asn Asn Gln Leu Asp Gly Gln Ile Asp Asp Arg Phe Gly Asn Leu Met
            275                 280                 285

Tyr Leu Glu His Leu Asn Leu Ala Asn Glu Leu Asn Leu Lys Gly Gly
        290                 295                 300

Ile Pro Ser Ser Phe Gly Asn Leu Thr Arg Leu Arg Tyr Leu Asp Met
305                 310                 315                 320

Ser Asn Thr Arg Thr Tyr Gln Trp Leu Pro Glu Leu Phe Val Arg Leu
                325                 330                 335

Ser Gly Ser Arg Lys Thr Leu Glu Val Leu Gly Leu Asn Asp Asn Ser
                340                 345                 350

Met Phe Gly Ser Leu Val Asp Val Thr Arg Phe Ser Ala Leu Lys Arg
            355                 360                 365

Leu Tyr Leu Gln Lys Asn Val Leu Asn Gly Phe Phe Met Glu Arg Phe
        370                 375                 380

Gly Gln Val Ser Ser Leu Glu Tyr Leu Asp Leu Ser Asp Asn Gln Met
385                 390                 395                 400

Arg Gly Pro Leu Pro Asp Leu Ala Leu Phe Pro Ser Leu Arg Glu Leu
                405                 410                 415

His Leu Gly Ser Asn His Phe Asn Gly Arg Ile Pro Gln Gly Ile Gly
                420                 425                 430

Lys Leu Ser Gln Leu Lys Ile Leu Asp Val Ser Ser Asn Arg Leu Glu
            435                 440                 445

Gly Leu Pro Glu Ser Met Gly Gln Leu Ser Asn Leu Glu Ser Phe Asp
        450                 455                 460

Ala Ser Tyr Asn Val Leu Lys Gly Thr Ile Thr Glu Ser His Leu Ser
465                 470                 475                 480

Asn Leu Ser Ser Leu Val Asp Leu Asp Leu Ser Phe Asn Ser Leu Ala
                485                 490                 495

Leu Lys Thr Ser Ile Asp Trp Leu Pro Pro Phe Gln Leu Gln Val Ile
                500                 505                 510

Asn Leu Pro Ser Cys Asn Leu Gly Pro Ser Phe Pro Lys Trp Leu Gln
            515                 520                 525

Ser Gln Asn Asn Tyr Thr Val Leu Asp Ile Ser Leu Ala Asn Ile Ser
        530                 535                 540

Asp Ala Leu Pro Ser Trp Phe Ser Gly Leu Pro Asp Ile Lys Ile
545                 550                 555                 560

Leu Asn Leu Ser Asn Asn Gln Ile Ser Gly Arg Val Ser Asp Leu Ile
                565                 570                 575

Glu Asn Ala Tyr Asp Tyr Met Val Ile Asp Leu Ser Ser Asn Asn Phe
                580                 585                 590

Ser Gly Pro Leu Pro Leu Val Pro Thr Asn Val Gln Ile Phe Tyr Leu
            595                 600                 605

His Lys Asn Gln Phe Phe Gly Ser Ile Ser Ile Cys Lys Ser Thr
        610                 615                 620

Thr Gly Ala Thr Ser Leu Asp Leu Ser His Asn Gln Phe Ser Gly Glu
625                 630                 635                 640
```

Leu Pro Asp Cys Trp Met Asn Ala Thr Asn Leu Ala Val Leu Asn Leu
                645                 650                 655

Ala Tyr Asn Asn Phe Ser Gly Lys Leu Pro Gln Ser Leu Gly Ser Leu
            660                 665                 670

Thr Asn Leu Glu Ala Leu Tyr Met Arg Gln Asn Ser Phe Ser Gly Met
        675                 680                 685

Leu Pro Ser Leu Ser Gln Cys Gln Ser Leu Gln Ile Leu Asp Leu Gly
    690                 695                 700

Gly Asn Lys Leu Thr Gly Arg Ile Pro Ala Trp Ile Gly Thr Asp Leu
705                 710                 715                 720

Leu Asn Leu Arg Ile Leu Ser Leu Arg Phe Asn Lys Phe Tyr Gly Ser
                725                 730                 735

Ile Ser Pro Ile Ile Cys Gln Leu Gln Phe Leu Gln Ile Leu Asp Leu
            740                 745                 750

Ser Ala Asn Gly Leu Ala Gly Lys Ile Pro Gln Cys Phe Asn Asn Phe
        755                 760                 765

Thr Leu Leu His Gln Glu Asn Gly Leu Gly Glu Pro Met Glu Phe Leu
    770                 775                 780

Val Gln Gly Phe Tyr Gly Lys Tyr Pro Arg His Tyr Ser Tyr Leu Gly
785                 790                 795                 800

Asn Leu Leu Val Gln Trp Lys Asn Gln Glu Ala Glu Tyr Lys Asn Pro
                805                 810                 815

Leu Thr Tyr Leu Lys Thr Ile Asp Leu Ser Ser Asn Lys Leu Val Gly
            820                 825                 830

Gly Ile Pro Lys Glu Met Ala Glu Met Arg Gly Leu Lys Ser Leu Asn
        835                 840                 845

Leu Ser Arg Asn Asp Leu Asn Gly Ser Ile Ile Lys Gly Ile Gly Gln
    850                 855                 860

Met Lys Met Leu Glu Ser Leu Asp Leu Ser Arg Asn Gln Leu Ser Gly
865                 870                 875                 880

Met Ile Pro Lys Asp Leu Ala Asn Leu Thr Phe Ile Gly Val Leu Asp
                885                 890                 895

Leu Ser Asn Asn His Leu Ser Gly Arg Ile Pro Ser Ser Thr Gln Leu
            900                 905                 910

Gln Thr Phe Glu Arg Ser Ser Tyr Ser Gly Asn Ala Gln Leu Cys Gly
        915                 920                 925

Pro Pro Leu Gln Glu Cys Pro Gly Tyr Ala Pro Ser Pro Arg Ile
    930                 935                 940

Asp His Asn Ser Asn Met Asn Pro Gln Glu Leu Asp Val Asp Asp
945                 950                 955                 960

Phe Pro Ser Leu Glu Phe Tyr Ile Ser Met Val Leu Gly Phe Phe Val
                965                 970                 975

Ala Phe Trp Gly Ile Leu Gly Ser Leu Ile Val Asn His Ser Trp Arg
            980                 985                 990

Asn Ala Tyr Phe Ile Phe Leu Met Asp Thr Lys Asn Trp Leu Ala Met
        995                 1000                1005

Ile Ser Arg Val Cys Cys Ser Arg Leu Lys Arg Lys Leu Arg Ala
    1010                1015                1020

<210> SEQ ID NO 4
<211> LENGTH: 1032
<212> TYPE: PRT
<213> ORGANISM: Artificial Sequence
<220> FEATURE:

<223> OTHER INFORMATION: recombinant protein

<400> SEQUENCE: 4

```
Met Asp Lys Arg Lys Tyr Pro Arg Leu Asp His Phe Leu Val Thr Trp
1               5                   10                  15

Ser Leu Leu Leu Leu Gln Thr Ala Leu Gly Leu Thr Ser Arg Glu Val
            20                  25                  30

Asn Lys Thr Met Cys Ile Gln Lys Glu Arg Asp Ala Leu Leu Glu Phe
                35                  40                  45

Lys Arg Gly Leu Ile Asp Asp Phe Asp Arg Leu Ser Thr Trp Gly Asp
        50                  55                  60

Glu Glu Asp Lys Lys Glu Cys Cys Lys Trp Lys Gly Ile Glu Cys Asp
65                  70                  75                  80

Lys Arg Ser Gly His Val Thr Val Leu Asp Leu His Thr Glu Val Ser
                85                  90                  95

Cys Pro Val Arg Ser Cys Phe Ala Pro Met Leu Thr Gly Lys Leu Ser
            100                 105                 110

Pro Ser Leu Leu Glu Leu His His Leu Asn Tyr Leu Asp Leu Ser His
                115                 120                 125

Asn Gly Phe Asp Lys Ile Glu Ile Pro Arg Phe Ile Ser Ser Leu Lys
        130                 135                 140

Arg Leu Glu Tyr Leu Asn Leu Ser Ser Ser Asp Phe Ser Gly Val Ile
145                 150                 155                 160

Pro Thr Gln Leu Lys Asn Leu Thr Ser Leu Arg Ile Leu Asp Leu Gly
                165                 170                 175

Asn Asn Asn Gln Leu Ile Val Lys Asp Leu Gly Trp Leu Ser Tyr Leu
            180                 185                 190

Ser Ser Leu Glu Ile Leu Arg Leu Gly Gly Asn Asp Phe Gln Ala Ser
        195                 200                 205

Asn Trp Phe Gln Glu Ile Thr Lys Val Pro Ser Leu Lys Glu Leu Asp
    210                 215                 220

Leu Ser Val Cys Gly Leu Ser Lys Phe Val Pro Ser Pro Ala Asp Leu
225                 230                 235                 240

Val Lys Ser Ser Leu Ile Ser Leu Ser Val Leu His Leu Cys Cys Asn
                245                 250                 255

Gln Phe Thr Ser Ser Ala Glu Tyr Ser Trp Leu Phe Asn Phe Ser Thr
            260                 265                 270

Ser Leu Thr Ser Ile Asp Leu Ser Asn Asn Gln Leu Asp Gly Pro Ile
        275                 280                 285

Asp Asp Arg Phe Gly Ser Leu Met Tyr Leu Glu His Leu Lys Leu Ala
    290                 295                 300

Asp Gln Phe Asn Leu Lys Gly Val Gly Val Pro Ser Ser Phe Gly Asn
305                 310                 315                 320

Leu Thr Arg Leu Arg Tyr Leu Asp Ile Ser Thr Arg Thr Tyr Gln
                325                 330                 335

Trp Leu Pro Glu Leu Phe Leu Arg Leu Ser Gly Ser Arg Lys Thr Leu
            340                 345                 350

Glu Val Leu Gly Leu Asn Asp Asn Ser Met Phe Gly Ser Leu Val Asn
        355                 360                 365

Val Thr Arg Phe Ser Ala Leu Lys Arg Leu Tyr Leu Gln Asn Asn Val
    370                 375                 380

Leu Asn Gly Phe Phe Met Glu Arg Phe Gly Gln Val Ser Ser Leu Glu
385                 390                 395                 400
```

```
Tyr Leu Asp Leu Ser Asp Asn Gln Met Arg Gly Ser Leu Pro Asp Leu
            405                 410                 415

Ala Leu Phe Pro Ser Met Arg Glu Leu His Leu Gly Ser Asn Gln Phe
        420                 425                 430

Gln Gly Arg Ile Pro Gln Gly Ile Gly Lys Leu Ser Gln Leu Arg Ile
        435                 440                 445

Leu Asp Val Ser Ser Asn Arg Leu Glu Gly Leu Pro Glu Ser Met Gly
450                 455                 460

Gln Leu Ser Asn Leu Glu Ser Phe Asp Ala Ser Tyr Asn Ala Leu Lys
465                 470                 475                 480

Gly Thr Ile Thr Glu Ser His Leu Ser Asn Leu Ser Ser Leu Val Tyr
                485                 490                 495

Leu Asp Leu Ser Phe Asn Ser Leu Ala Leu Lys Thr Ser Phe Asp Trp
            500                 505                 510

Leu Pro Pro Phe Gln Leu Gln Phe Ile Asn Leu Pro Ser Cys Asn Leu
        515                 520                 525

Gly Pro Ser Phe Pro Lys Trp Leu Gln Ser Gln Asn Asn Tyr Thr Val
        530                 535                 540

Leu Asp Ile Ser Leu Ala Asn Leu Ser Asp Ala Leu Pro Ser Trp Phe
545                 550                 555                 560

Ser Asp Leu Pro Leu Asn Leu Lys Ile Leu Asn Leu Ser Asn Asn His
                565                 570                 575

Ile Ser Gly Arg Val Ser Glu Phe Ile Val Asn Lys Gln Asp Tyr Met
            580                 585                 590

Val Ile Asp Leu Ser Ser Asn Asn Phe Ser Gly Pro Leu Pro Leu Val
        595                 600                 605

Pro Ile Asn Val Arg Ile Phe Tyr Leu His Lys Asn Lys Phe Ser Gly
        610                 615                 620

Ser Thr Ser Ser Ile Cys Lys Ser Thr Thr Gly Gly Ala Thr Ser Val
625                 630                 635                 640

Asp Leu Ser His Asn Gln Phe Ser Gly Glu Leu Pro Asp Cys Trp Met
                645                 650                 655

Asn Met Ser Asn Leu Val Val Leu Asn Leu Ala Tyr Asn Asn Phe Ser
            660                 665                 670

Gly Lys Leu Pro Gln Ser Leu Gly Ser Leu Glu Ser Leu Glu Ala Leu
        675                 680                 685

Tyr Ile Arg Gln Asn Ser Phe Asn Gly Met Leu Pro Ser Phe Ser Gln
        690                 695                 700

Cys Gln Ser Leu Gln Ile Leu Asp Leu Gly Gly Asn Lys Leu Thr Gly
705                 710                 715                 720

Arg Ile Pro Ala Trp Ile Gly Asn Asp Leu Leu Asn Leu Arg Ile Leu
                725                 730                 735

Ser Leu Arg Phe Asn Lys Phe Tyr Gly Ser Ile Pro Ser Ile Ile Cys
            740                 745                 750

Gln Leu Gln Phe Leu Gln Ile Leu Asp Ile Ser Ala Asn Gly Leu Ser
        755                 760                 765

Gly Lys Ile Pro Gln Cys Phe Asn Asn Phe Thr Leu Leu His Gln Glu
        770                 775                 780

Asn Gly Ser Gly Glu Ser Met Glu Phe Leu Val Gln Leu Asp Tyr Leu
785                 790                 795                 800

Pro Arg Ser Tyr Leu Tyr Ile Gly Asn Leu Leu Val Gln Trp Lys Asn
                805                 810                 815

Gln Glu Ala Glu Tyr Lys Asn Pro Leu Leu Tyr Leu Lys Ala Ile Asp
```

-continued

```
                    820                 825                 830
Leu Ser Ser Asn Lys Leu Val Gly Asn Ile Pro Lys Glu Ile Ala Glu
                835                 840                 845
Met Arg Gly Leu Lys Ser Leu Asn Leu Ser Arg Asn Asp Leu Asn Gly
            850                 855                 860
Ser Ile Ile Glu Gly Ile Gly Gln Met Lys Met Leu Glu Ser Leu Asp
865                 870                 875                 880
Leu Ser Arg Asn Gln Leu Ser Gly Met Ile Pro Lys Gly Leu Ala Asn
                885                 890                 895
Leu Thr Phe Ile Gly Val Leu Asp Leu Ser Asn Asn His Leu Ser Gly
            900                 905                 910
Arg Ile Pro Ser Ser Thr Gln Leu Gln Thr Phe Glu Thr Ser Ser Tyr
            915                 920                 925
Ser Gly Asn Ala Gln Leu Cys Gly Pro Pro Leu Glu Glu Cys Pro Gly
        930                 935                 940
Phe Ala Pro Pro Ser Pro Arg Ile Asn His Gly Ser Asn Ile Asn Pro
945                 950                 955                 960
Gln Glu Leu Gly Asp Asp Asp Glu Phe Pro Ser Leu Glu Phe Tyr Ile
                965                 970                 975
Ser Met Val Leu Gly Phe Val Ala Phe Trp Gly Ile Leu Gly Cys
            980                 985                 990
Leu Ile Val Asn Arg Ala Trp Arg  Asn Ala Tyr Phe Thr  Phe Leu Met
                995                 1000                1005
Asp Thr  Lys Asn Trp Leu Ala  Met Ile Ser Arg Val  Cys Phe Thr
    1010                1015                1020
Arg Leu  Lys Gly Lys Leu Arg  Ala Ser
1025                 1030

<210> SEQ ID NO 5
<211> LENGTH: 578
<212> TYPE: PRT
<213> ORGANISM: Artificial Sequence
<220> FEATURE:
<223> OTHER INFORMATION: recombinant protein

<400> SEQUENCE: 5

Met Arg Gly Pro Leu Pro Asp Leu Ala Leu Phe Pro Ser Leu Arg Glu
1               5                   10                  15
Leu His Leu Gly Phe Gln Trp Arg Ile Pro Gln Glu Phe Trp Val Ser
                20                  25                  30
Ser Asn Arg Leu Glu Gly Leu Pro Lys Ser Met Gly Gln Leu Ser Asn
            35                  40                  45
Leu Glu Ser Ile Asp Ala Ser Tyr Asn Val Leu Lys Gly Ile Ile Ile
        50                  55                  60
Glu Ser His Leu Ser Asn Leu Ser Ser Leu Val Asp Leu Asp Leu Ser
65                  70                  75                  80
Phe Asn Ser Leu Ala Leu Lys Thr Ser Phe Asp Trp Leu Pro Pro Phe
                85                  90                  95
Gln Leu Gln Phe Ile Asn Leu Pro Ser Cys Asn Leu Gly Pro Ser Phe
                100                 105                 110
Pro Lys Trp Leu His Ser Gln Asn Asn Cys Thr Val Leu Glu Ile Ser
            115                 120                 125
Leu Ala Asn Leu Ser Asp Ala Leu Pro Ser Trp Phe Ser Asp Leu Pro
        130                 135                 140
Leu Asn Leu Lys Ile Leu Thr Leu Ser Asn Asn His Ile Ser Gly Arg
```

```
            145                 150                 155                 160
        Val Ser Glu Leu Ile Val Asn Lys Gln Asp Tyr Met Val Ile Asp Leu
                        165                 170                 175

Ser Ser Asn Asn Phe Ser Gly Pro Leu Pro Gln Val Pro Thr Asn Val
                        180                 185                 190

Arg Ile Phe Tyr Leu His Lys Asn Lys Phe Ser Gly Ser Thr Ser Ser
                        195                 200                 205

Ile Cys Lys Ser Thr Thr Gly Ala Ala Thr Ser Leu Asp Leu Ser His
                        210                 215                 220

Asn Leu Phe Ser Gly Glu Leu Pro Asp Cys Trp Met Asn Met Ser Asn
        225                 230                 235                 240

Leu Val Val Leu Asn Leu Ala Phe Asn Asn Phe Ser Gly Lys Leu Pro
                        245                 250                 255

His Gly Ile Leu Pro Ser Phe Ser Gln Cys Gln Leu Leu Gln Ile Leu
                        260                 265                 270

Asp Leu Gly Gly Asn Lys Leu Thr Gly Arg Ile Pro Ala Trp Ile Gly
                        275                 280                 285

Thr Asp Leu Leu Asn Leu Arg Ile Leu Ser Leu Arg Phe Asn Lys Phe
                        290                 295                 300

Tyr Gly Ser Ile Leu Phe Ile Ile Cys Gln Leu Gln Phe Leu Gln Ile
        305                 310                 315                 320

Leu Asp Leu Ser Ala Asn Gly Leu Ser Glu Gln Cys Phe Asn Asn Phe
                        325                 330                 335

Thr Leu Leu His Gln Glu Asn Gly Ser Gly Glu Ser Met Asn Phe Ser
                        340                 345                 350

Val Gln Tyr Asp Tyr Met Pro Arg Ser Tyr Leu Tyr Ile Gly Asn Leu
                        355                 360                 365

Leu Val Gln Trp Lys Asn Gln Glu Ala Glu Tyr Lys Asn Pro Leu Leu
                        370                 375                 380

Tyr Leu Lys Ala Ile Asp Leu Ser Ser Asn Lys Leu Val Gly Gly Ile
        385                 390                 395                 400

Pro Lys Glu Ile Ala Glu Met Arg Gly Leu Lys Ser Leu Asn Leu Ser
                        405                 410                 415

Arg Asn Asp Leu Asn Gly Ser Ile Ile Glu Gly Ile Gly Gln Met Lys
                        420                 425                 430

Met Leu Glu Ser Leu Asp Leu Ser Arg Asn Gln Leu Ser Gly Met Ile
                        435                 440                 445

Pro Lys Asp Leu Ala Asn Leu Thr Phe Ile Gly Val Leu Asp Leu Ser
                        450                 455                 460

Asn Asn His Leu Ser Gly Arg Ile Pro Ser Ser Thr Gln Leu Gln Thr
        465                 470                 475                 480

Phe Glu Arg Ser Ser Tyr Ser Gly Asn Ala Lys Leu Cys Gly Pro Pro
                        485                 490                 495

Leu Gln Glu Cys Pro Gly Tyr Ala Pro Pro Ser Pro Cys Ile Asp His
                        500                 505                 510

Asn Ser Asn Met Asn Pro Gln Glu Leu Asp Asp Asp Asp Phe Pro
                        515                 520                 525

Ser Leu Glu Phe Tyr Ile Ser Met Val Leu Gly Phe Phe Val Ala Phe
                        530                 535                 540

Trp Gly Ile Leu Gly Ser Leu Ile Val Asn His Ser Trp Arg Asn Ala
        545                 550                 555                 560

Tyr Phe Ile Phe Leu Met Asp Val Lys Asn Trp Leu Ala Met Ile Ser
                        565                 570                 575
```

Arg Val

<210> SEQ ID NO 6
<211> LENGTH: 44
<212> TYPE: DNA
<213> ORGANISM: Artificial Sequence
<220> FEATURE:
<223> OTHER INFORMATION: upstream primer

<400> SEQUENCE: 6
ttacgaacga tagccggtac catgggcaaa agggaatatc caag          44

<210> SEQ ID NO 7
<211> LENGTH: 44
<212> TYPE: DNA
<213> ORGANISM: Artificial Sequence
<220> FEATURE:
<223> OTHER INFORMATION: downstream primer

<400> SEQUENCE: 7
gctcaccatc ccgggggtac cagcccttaa ctttctcttc agtc          44

<210> SEQ ID NO 8
<211> LENGTH: 36
<212> TYPE: DNA
<213> ORGANISM: Artificial Sequence
<220> FEATURE:
<223> OTHER INFORMATION: upstream primer

<400> SEQUENCE: 8
cgacaagacc ctgcaggttt caagagataa ctaaac               36

<210> SEQ ID NO 9
<211> LENGTH: 35
<212> TYPE: DNA
<213> ORGANISM: Artificial Sequence
<220> FEATURE:
<223> OTHER INFORMATION: downstream primer

<400> SEQUENCE: 9
gagaagagcc ctgcagaaga attggctatt tcagc                35

<210> SEQ ID NO 10
<211> LENGTH: 23
<212> TYPE: DNA
<213> ORGANISM: Artificial Sequence
<220> FEATURE:
<223> OTHER INFORMATION: forward primer

<400> SEQUENCE: 10
gctccttaac aaatttagag gcg                             23

<210> SEQ ID NO 11
<211> LENGTH: 23
<212> TYPE: DNA
<213> ORGANISM: Artificial Sequence
<220> FEATURE:
<223> OTHER INFORMATION: reverse primer

<400> SEQUENCE: 11
tgattggtga aatgctgcca tag                             23

<210> SEQ ID NO 12
<211> LENGTH: 9613
<212> TYPE: DNA

<213> ORGANISM: Artificial Sequence
<220> FEATURE:
<223> OTHER INFORMATION: gene expression vector

<400> SEQUENCE: 12

```
atgcttgaca ctttatcact gataaacata atatgtccac caacttatca gtgataaaga      60
atccgcgcgt tcaatcggac cagcggaggc tggtccggag gccagacgtg aaacccaaca     120
taccccctgat cgtaattctg agcactgtcg cgctcgacgc tgtcggcatc ggcctgatta    180
tgccggtgct gccgggcctc ctgcgcgatc tggttcactc gaacgacgtc accgcccact    240
atggcattct gctggcgctg tatgcgttgg tgcaatttgc ctgcgcacct gtgctgggcg    300
cgctgtcgga tcgtttcggg cggcggccaa tcttgctcgt ctcgctggcc ggcgccagat    360
ctggggaacc ctgtggttgg catgcacata caaatggacg aacggataaa ccttttcacg    420
cccttttaaa tatccgatta ttctaataaa cgctcttttc tcttaggttt acccgccaat    480
atatcctgtc aaacactgat agtttgtgaa ccatcaccca aatcaagttt tttggggtcg    540
aggtgccgta aagcactaaa tcggaaccct aaagggagcc cccgatttag agcttgacgg    600
ggaaagccgg cgaacgtggc gagaaaggaa gggaagaaag cgaaaggagc gggcgccatt    660
caggctgcgc aactgttggg aagggcgatc ggtgcgggcc tcttcgctat tacgccagct    720
ggcgaaaggg ggatgtgctg caaggcgatt aagttgggta acgccagggt tttcccagtc    780
acgacgttgt aaaacgacgg ccagtgaatt gttaattaag aattcgagct ccttgcatgc    840
ctgcaggtca acatggtgga gcacgacaca cttgtctact ccaaaaatat caaagataca    900
gtctcagaag accaaagggc aattgagact tttcaacaaa gggtaatatc cggaaacctc    960
ctcggattcc attgcccagc tatctgtcac tttattgtga agatagtgga aaaggaaggt   1020
ggctcctaca aatgccatca ttgcgataaa ggaaaggcca tcgttgaaga tgcctctgcc   1080
gacagtggtc ccaaagatgg acccccaccc acgaggagca tcgtggaaaa agaagacgtt   1140
ccaaccacgt cttcaaagca agtggattga tgtgataaca tggtggagca cgacacactt   1200
gtctactcca aaaatatcaa agatacagtc tcagaagacc aaagggcaat tgagactttt   1260
caacaaaggg taatatccgg aaacctcctc ggattccatt gcccagctat ctgtcacttt   1320
attgtgaaga tagtggaaaa ggaaggtggc tcctacaaat gccatcattg cgataaagga   1380
aaggccatcg ttgaagatgc tctgccgac agtggtccca aagatggacc cccacccacg    1440
aggagcatcg tggaaaaaga gacgttcca accacgtctt caaagcaagt ggattgatgt   1500
gatatctcca ctgacgtaag ggatgacgca caatcccact atccttcgca agacccttcc   1560
tctatataag gaagttcatt tcatttggag aggacctcga gaattctcaa cacaacatat   1620
acaaaacaaa cgaatctcaa gcaatcaagc attctacttc tattgcagca atttaaatca   1680
tttcttttaa agcaaaagca attttctgaa aattttcacc atttacgaac gatagccggt   1740
accatgggca aaagggaata tccaagttca gctcatttcc ttgttacttt gtctttactg   1800
ctcctacaag cagcttttgg attgactctg tgtatagaaa aggagagaga tgcccttctt   1860
gaattcaaaa gaggtcttag tgataatttt ggtcaattat caacatgggg tgatgaagaa   1920
gataaaaaag aatgttgcaa atggaaaggt attgaatgta acaaaacaac cggtcatgta   1980
attgttcttg atcttcataa tgcctttact tgttctgcta gtgcttgttt tgctccaaga   2040
ttgacaggta aacttagtcc ttctttactt gagttggagt atttgaattt cttggacctt   2100
agtgtgaatg aatttgaaag aagtgaaata ccaagattca tatgctcctt taagagacta   2160
gagtatttga acctctcatc ttcctttttt tctggtttaa ttcctacaca gttcaagaat   2220
```

```
ctaacttcat tgaggattct tgatcttgga tataataatc ttatagtaaa ggaccttaca    2280
tggctttctc atctctcttc tctagagtta ttgagtctag gtggtagtga cttccaagta    2340
aagaattggt ttcaagagat aactaaactt cctttattga agaacttga cttgagtctt     2400 tgtggactct ctaaattagt tccatctcca gctgaaatag ccaattcttc tttgatctct    2460
ctttctgttc ttcatttatg ttgtaatgag ttttcttctt cagctaaata tagctggttg    2520
ttcaatttta gcacaagctt aactagtata gacctctcaa ataatcagct agacggtcaa    2580
attgatgatc gatttgggaa cttgatgtat cttgaacatc ttaatcttgc aaatgagctt    2640
aatcttaaag gtgggattcc aagttctttt ggcaatttga cacgtttacg ttatctggac    2700
atgtctaaca ctcgaacata ccaatggctt cctgagttgt tgtcagatt atcaggcagt     2760 aggaaaacac ttgaggtttt ggggttgaac gacaactcaa tgtttggttc attggttgat    2820
gtcacaagat tttcagcctt aaagagatta tacctgcaga aaaatgtgct gaatggtttt    2880
ttcatggaaa gatttggaca agtttcgagc cttgagtatc tagacttatc tgataaccaa    2940
atgagagggc cattaccaga tttagcattg tttccatcat tgagagagtt gcatctcgga    3000
tctaatcact tcaatgggag gataccacaa ggtattggaa aactttcaca gcttaaaatt    3060
ttggacgtct cgtccaatag gctggaagga ttaccagaaa gtatggggca gctgtcgaac    3120
ctggaaagtt ttgatgcctc ttacaatgtc ctgaagggta caatcactga gtcccacctt    3180
tcaaatctct ccagtttagt ggatttggac ttatcgttca actcgttggc tttgaagacg    3240
agcatcgatt ggcttcctcc ttttcagctt caagttataa accttccatc ttgcaatttg    3300
ggaccttctt tccccaagtg gcttcaaagt caaacaatt atactgttct tgatatctct    3360
cttgcaaata tttcagacgc gcttccaagt tggttctcag gtttacctcc cgatataaag    3420
attttgaatc tctccaacaa ccaaatcagt ggaagagtat ctgacttaat agagaatgca    3480
tatgattaca tggtaataga tttaagctct aacaacttt caggacctt gccattagtt      3540 cctaccaatg tgcaaatatt ttacctgcac aaaaatcagt ttttcggatc catctcttcc    3600
atttgtaaaa gtacaacagg agccacttcc cttgacctat cacacaacca attctcagga    3660
gagcttcctg attgttggat gaatgcgact aatctagctg ttcttaatct agcctataac    3720
aatttctctg gaaaacttcc acagtcatta ggctccttaa caaatttaga ggcgttatac    3780
atgcgccaga acagttttag tggaatgttg ccttctttat cacaatgtca gtctttgcaa    3840
atcttggatc ttggaggaaa taagctgaca ggaagaatcc cagcatggat agggactgac    3900
ctactcaact tgcgcattct aagcctgcgg ttcaacaaat tctatggcag catttccacca    3960 atcatttgtc agcttcagtt tcttcagata ctggaccttt cagcaaatgg tttagctggc    4020
aaaattccac aatgcttcaa taattttacc ttactgcatc aagaaaatgg tttgggcgag    4080
ccaatggaat ttctagttca aggtttctat ggcaaatatc ctcgacatta ctcgtaccta    4140
ggcaatttat tggttcaatg gaaaaaccag gaggctgagt acaagaatcc tttaacatat    4200
ctgaagacta ttgatctttc aagtaacaag ttggttggag gtatccctaa agaaatggct    4260
gaaatgagag gattgaaatc tttgaacctt tcacgaaatg atctgaatgg aagtatcatt    4320
aaaggaatag gtcaaatgaa gatgttggag tcacttgacc tgtcaagaaa ccagcttct     4380 ggtatgattc ctaaagacct tgctaacttg actttattg gtgtgttgga cttgtcaaac    4440
aaccacttat cagggagaat tccatcaagc actcaactcc aaactttga gagatcatcc     4500 tacagtggta acgctcaact ctgcggtcct cctcttcaag aatgtcccgg atatgctccc    4560
```

```
cctagcccac gtatcgatca taacagcaac atgaatcctc aagaacttga cgttgatgat    4620
gattttccat ctctggagtt ttatatatcg atggtgctag gtttctttgt tgcattctgg    4680
ggaatcttgg gctcttaat tgtcaatcat tcttggagga atgcctactt catattctta    4740
atggacacga agaattggct cgctatgata tcaagagtct gttgttcaag actgaagaga    4800
aagttaaggg ctggtacccc cgggatggtg agcaagggcg aggagctgtt caccggggtg    4860
gtgcccatcc tggtcgagct ggacggcgac gtaaacggcc acaagttcag cgtgtccggc    4920
gagggcgagg gcgatgccac ctacggcaag ctgaccctga agttcatctg caccaccggc    4980
aagctgcccg tgccctggcc caccctcgtg accaccctga cctacggcgt gcagtgcttc    5040
agccgctacc ccgaccacat gaagcagcac gacttcttca gtccgccat gcccgaaggc    5100 tacgtccagg agcgcaccat cttcttcaag gacgacggca actacaagac ccgcgccgag    5160
gtgaagttcg agggcgacac cctggtgaac cgcatcgagc tgaagggcat cgacttcaag    5220
gaggacggca acatcctggg gcacaagctg gagtacaact acaacagcca caacgtctat    5280
atcatggccg acaagcagaa gaacggcatc aaggtgaact tcaagatccg ccacaacatc    5340
gaggacggca gcgtgcagct cgccgaccac taccagcaga acacccccat cggcgacggc    5400
cccgtgctgc tgcccgacaa ccactacctg agcacccagt ccgccctgag caaagacccc    5460
aacgagaagc gcgatcacat ggtcctgctg gagttcgtga ccgccgccgg gatcactctc    5520
ggcatggacg agctgtacaa gtaaggatcc tctagatgaa ctagagtccg caaaaatcac    5580
cagtctctct ctacaaatct atctctctct attttctcc agaataatgt gtgagtagtt    5640
cccagataag ggaattaggg ttcttatagg gtttcgctca tgtgttgagc atataagaaa    5700
cccttagtat gtatttgtat ttgtaaaata cttctatcaa taaaatttct aattcctaaa    5760
accaaaatcc agtgacaagc ttggcgcgcc agcttggcgt aatcatggtc atagctgttt    5820
cctgtgtgaa attgttatcc gctcacaatt ccacacaaca tacgagccgg aagcataaag    5880
tgtaaagcct ggggtgccta atgagtgagc taactcacat taattgcgtt gcgctcactg    5940
cccgctttcc agtcgggaaa cctgtcgtgc cagctgcatt aatgaatcgg ccaacgcgcg    6000
gggagaggcg gtttgcgtat tgggccaaag acaaaagggc gacattcaac cgattgaggg    6060
agggaaggta atattgacg gaaattattc attaaaggtg aattatcacc gtcaccgact    6120
tgagccattt gggaattaga gccagcaaaa tcaccagtag caccattacc attagcaagg    6180
ccggaaacgt caccaatgaa accatcgata gcagcaccgt aatcagtagc gacagaatca    6240
agtttgcctt tagcgtcaga ctgtagcgcg ttttcatcgg catttccggt catagccccc    6300
ttattagcgt ttgccatctt ttcataatca aaatcaccgg aaccagagcc accaccggaa    6360
ccgcctccct cagagccgcc accctcgaaa ccgccaccct cagagccacc accctcagag    6420
ccgccaccag aaccaccacc agagccgccg ccagcattga caggaggccc gatctagtaa    6480
catagatgac accgcgcgcg ataatttatc ctagtttgcg cgctatattt tgttttctat    6540
cgcgtattaa atgtataatt gcgggactct aatcataaaa acccatctca taaataacgt    6600
catgcattac atgttaatta ttacatgctt aacgtaattc aacagaaatt atatgataat    6660
catcgcaaga ccggcaacag gattcaatct taagaaactt tattgccaaa tgtttgaacg    6720
atcggggatc atccgggtct gtggcgggaa ctccacgaaa atatccgaac gcagcaagat    6780
atcgcggtgc atctccggtct tgcctgggca gtcgccgccg acgccgttga tgtggacgcc    6840
gggcccgatc atattgtcgc tcaggatcgt ggcgttgtgc ttgtcggccg ttgctgtcgt    6900
aatgatatcg gcaccttcga ccgcctgttc cgcagagatc ccgtgggcga agaactccag    6960
```

| | |
|---|---|
| catgagatcc ccgcgctgga ggatcatcca gccggcgtcc cggaaaacga ttccgaagcc | 7020 |
| caacctttca tagaaggcgg cggtggaatc gaaatctcgt gatggcaggt tgggcgtcgc | 7080 |
| ttggtcggtc atttcgaacc ccagagtccc gctcagaaga actcgtcaag aaggcgatag | 7140 |
| aaggcgatgc gctgcgaatc gggagcggcg ataccgtaaa gcacgaggaa gcggtcagcc | 7200 |
| cattcgccgc caagctcttc agcaatatca cgggtagcca acgctatgtc ctgatagcgg | 7260 |
| tccgccacac ccagccggcc acagtcgatg aatccagaaa agcggccatt ttccaccatg | 7320 |
| atattcggca agcaggcatc gccatgggtc acgacgagat catcgccgtc gggcatgcgc | 7380 |
| gccttgagcc tggcgaacag ttcggctggc gcgagcccct gatgctcttc gtccagatca | 7440 |
| tcctgatcga caagaccggc ttccatccga gtacgtgctc gctcgatgcg atgtttcgct | 7500 |
| tggtggtcga atgggcaggt agccggatca agcgtatgca gccgccgcat tgcatcagcc | 7560 |
| atgatggata ctttctcggc aggagcaagg tgagatgaca ggagatcctg ccccggcact | 7620 |
| tcgcccaata gcagccagtc ccttcccgct tcagtgacaa cgtcgagcac agctgcgcaa | 7680 |
| ggaacgcccg tcgtggccag ccacgatagc cgcgctgcct cgtcctgcag ttcattcagg | 7740 |
| gcaccggaca ggtcggtctt gacaaaaaga accgggcgcc cctgcgctga cagccggaac | 7800 |
| acggcggcat cagagcagcc gattgtctgt tgtgcccagt catagccgaa tagcctctcc | 7860 |
| acccaagcgg ccggagaacc tgcgtgcaat ccatcttgtt caatcatgcg aaacgatcca | 7920 |
| gatccggtgc agattatttg gattgagagt gaatatgaga ctctaattgg ataccgaggg | 7980 |
| gaatttatgg aacgtcagtg gagcattttt gacaagaaat atttgctagc tgatagtgac | 8040 |
| cttaggcgac ttttgaacgc gcaataatgg tttctgacgt atgtgcttag ctcattaaac | 8100 |
| tccagaaacc cgcggctgag tggctccttc aacgttgcgg ttctgtcagt tccaaacgta | 8160 |
| aaacggcttg tcccgcgtca tcggcgggg tcataacgtg actcccttaa ttctccgctc | 8220 |
| atgatcagat tgtcgtttcc cgccttcagt ttgtgggcca tcgccctgat agacggtttt | 8280 |
| tcgccctttg acgttggagt ccacgttctt taatagtgga ctcttgttcc aaactggaac | 8340 |
| aacactcaac cctatctcgg gctattcttt tgatttataa gggattttgc cgatttcgga | 8400 |
| accaccatca acaggatttt cgcctgctg gggcaaacca gcgtggaccg cttgctgcaa | 8460 |
| ctctctcagg gccaggcggt gaagggcaat cagctgttgc ccgtctcact ggtgaaaaga | 8520 |
| aaaaccaccc cagtacatta aaaacgtccg caatgtgtta ttaagttgtc taagcgtcaa | 8580 |
| tttgtttaca ccacaatata tcctgccacc agccagccaa cagctccccg accggcagct | 8640 |
| cggcacaaaa tcaccactcg atacaggcag cccatcagtc cgggacgcg tcagcgggag | 8700 |
| agccgttgta aggcggcaga ctttgctcat gttaccgatg ctattcggaa gaacggcaac | 8760 |
| taagctgccg ggtttgaaac acggatgatc tcgcggaggg tagcatgttg attgtaacga | 8820 |
| tgacagagcg ttgctgcctg tgatcaaata tcatctccct cgcagagatc cgaattatca | 8880 |
| gccttcttat tcatttctcg cttaaccgtg acaggctgtc gatcttgaga actatgccga | 8940 |
| cataatagga aatcgctgga taaagccgct gaggaagctg agtggcgcta tttctttaga | 9000 |
| agtgaacgtt gacgatatca actcccctat ccattgctca ccgaatggta caggtcgggg | 9060 |
| acccgaagtt ccgactgtcg gcctgatgca tccccggctg atcgacccca gatctggggc | 9120 |
| tgagaaagcc cagtaaggaa acaactgtag gttcgagtcg cgagatcccc cggaaccaaa | 9180 |
| ggaagtaggt taaacccgct ccgatcaggc cgagccacgc caggccgaga acattggttc | 9240 |
| ctgtaggcat cgggattggc ggatcaaaca ctaaagctac tggaacgagc agaagtcctc | 9300 |

| | |
|---|---|
| cggccgccag ttgccaggcg gtaaaggtga gcagaggcac gggaggttgc cacttgcggg | 9360 |
| tcagcacggt tccgaacgcc atggaaaccg ccccgccag gccgctgcg acgccgacag | 9420 |
| gatctagcgc tgcgtttggt gtcaacacca acagcgccac gcccgcagtt ccgcaaatag | 9480 |
| cccccaggac cgccatcaat cgtatcgggc tacctagcag agcggcagag atgaacacga | 9540 |
| ccatcagcgg ctgcacagcg cctaccgtcg ccgcgacccc gcccggcagg cggtagaccg | 9600 |
| aaataaacaa caa | 9613 |

<210> SEQ ID NO 13
<211> LENGTH: 6397
<212> TYPE: DNA
<213> ORGANISM: Artificial Sequence
<220> FEATURE:
<223> OTHER INFORMATION: partial vector sequence

<400> SEQUENCE: 13

| | |
|---|---|
| atgcttgaca ctttatcact gataaacata atatgtccac caacttatca gtgataaaga | 60 |
| atccgcgcgt tcaatcggac cagcggaggc tggtccggag ccagacgtg aaacccaaca | 120 |
| taccctgat cgtaattctg agcactgtcg cgctcgacgc tgtcggcatc ggcctgatta | 180 |
| tgccggtgct gccgggcctc ctgcgcgatc tggttcactc gaacgacgtc accgcccact | 240 |
| atggcattct gctggcgctg tatgcgttgg tgcaatttgc ctgcgcacct gtgctgggcg | 300 |
| cgctgtcgga tcgtttcggg cggcggccaa tcttgctcgt ctcgctgccg gcgccagat | 360 |
| ctggggaacc ctgtggttgg catgcacata caaatggacg aacggataaa ccttttcacg | 420 |
| cccttttaaa tatccgatta ttctaataaa cgctcttttc tcttaggttt acccgccaat | 480 |
| atatcctgtc aaacactgat agtttgtgaa ccatcaccca atcaagtttt ttggggtcg | 540 |
| aggtgccgta agcactaaa tcggaaccct aagggagcc cccgatttag agcttgacgg | 600 |
| ggaaagccgg cgaacgtggc gagaaaggaa gggaagaaag cgaaaggagc gggcgccatt | 660 |
| caggctgcgc aactgttggg aagggcgatc ggtgcgggcc tcttcgctat tacgccagct | 720 |
| ggcgaaaggg ggatgtgctg caaggcgatt aagttgggta acgccagggt tttcccagtc | 780 |
| acgacgttgt aaaacgacgg ccagtgaatt gttaattaag aattcgagct ccttgcatgc | 840 |
| ctgcaggtca acatggtgga gcacgacaca cttgtctact ccaaaaatat caaagataca | 900 |
| gtctcagaag accaaagggc aattgagact tttcaacaaa gggtaatatc cggaaacctc | 960 |
| ctcggattcc attgcccagc tatctgtcac tttattgtga agatagtgga aaggaaggt | 1020 |
| ggctcctaca aatgccatca ttgcgataaa ggaaaggcca tcgttgaaga tgcctctgcc | 1080 |
| gacagtggtc ccaaagatgg acccccaccc acgaggagca tcgtggaaaa agaagacgtt | 1140 |
| ccaaccacgt cttcaaagca agtggattga tgtgataaca tggtggagca cgacacactt | 1200 |
| gtctactcca aaaatatcaa agatacagtc tcagaagacc aaagggcaat tgagactttt | 1260 |
| caacaagggg taatatccgg aaacctcctc ggattccatt gcccagctat ctgtcacttt | 1320 |
| attgtgaaga tagtggaaaa ggaaggtggc tcctacaaat gccatcattg cgataaagga | 1380 |
| aaggccatcg ttgaagatgc ctctgccgac agtggtccca agatggacc cccacccacg | 1440 |
| aggagcatcg tggaaaaaga agacgttcca accacgtctt caaagcaagt ggattgatgt | 1500 |
| gatatctcca ctgacgtaag ggatgacgca caatcccact atccttcgca agacccttcc | 1560 |
| tctatataag gaagttcatt tcatttggag aggacctcga gaattctcaa cacaacatat | 1620 |
| acaaaacaaa cgaatctcaa gcaatcaagc attctacttc tattgcagca atttaaatca | 1680 |
| tttcttttaa agcaaaagca attttctgaa aattttcacc atttacgaac gatagccggt | 1740 |

```
accccccggga tggtgagcaa gggcgaggag ctgttcaccg gggtggtgcc catcctggtc    1800
gagctggacg gcgacgtaaa cggccacaag ttcagcgtgt ccggcgaggg cgagggcgat    1860
gccacctacg gcaagctgac cctgaagttc atctgcacca ccggcaagct gcccgtgccc    1920
tggcccaccc tcgtgaccac cctgacctac ggcgtgcagt gcttcagccg ctaccccgac    1980
cacatgaagc agcacgactt cttcaagtcc gccatgcccg aaggctacgt ccaggagcgc    2040
accatcttct tcaaggacga cggcaactac aagacccgcg ccgaggtgaa gttcgagggc    2100
gacaccctgg tgaaccgcat cgagctgaag ggcatcgact tcaaggagga cggcaacatc    2160
ctggggcaca gctggagtac aactacaac agccacaacg tctatatcat ggccgacaag    2220
cagaagaacg gcatcaaggt gaacttcaag atccgccaca acatcgagga cggcagcgtg    2280
cagctcgccg accactacca gcagaacacc cccatcggcg acggccccgt gctgctgccc    2340
gacaaccact acctgagcac ccagtccgcc ctgagcaaag accccaacga gaagcgcgat    2400
cacatggtcc tgctggagtt cgtgaccgcc gccgggatca ctctcggcat ggacgagctg    2460
tacaagtaag gatcctctag atgaactaga gtccgcaaaa atcaccagtc tctctctaca    2520
aatctatctc tctctatttt tctccagaat aatgtgtgag tagttcccag ataagggaat    2580
tagggttctt ataggggttc gctcatgtgt tgagcatata agaaacccttt agtatgtatt    2640 tgtatttgta aaatacttct atcaataaaa tttctaattc ctaaaaccaa aatccagtga    2700
caagcttggc gcgccagctt ggcgtaatca tggtcatagc tgtttcctgt gtgaaattgt    2760
tatccgctca caattccaca acaatacga gccggaagca taaagtgtaa agcctggggt    2820
gcctaatgag tgagctaact cacattaatt gcgttgcgct cactgcccgc tttccagtcg    2880
ggaaacctgt cgtgccagct gcattaatga atcggccaac gcgcggggag aggcggtttg    2940
cgtattgggc caaagacaaa agggcgacat tcaaccgatt gagggaggga aggtaaatat    3000
tgacggaaat tattcattaa aggtgaatta tcaccgtcac cgacttgagc catttgggaa    3060
ttagagccag caaaatcacc agtagcacca ttaccattag caaggccgga aacgtcacca    3120
atgaaaccat cgatagcagc accgtaatca gtagcgacag aatcaagttt gcctttagcg    3180
tcagactgta gcgcgttttc atcggcattt tcggtcatag cccccttatt agcgtttgcc    3240
atcttttcat aatcaaaatc accggaacca gagccaccac cggaaccgcc tccctcagag    3300
ccgccaccct cagaaccgcc accctcagag ccaccaccct cagagccgcc accagaacca    3360
ccaccagagc cgccgccagc attgacagga ggcccgatct agtaacatag atgacaccgc    3420
gcgcgataat ttatcctagt ttgcgcgcta tattttgttt tctatcgcgt attaaatgta    3480
taattgcggg actctaatca taaaaaccca tctcataaat aacgtcatgc attacatgtt    3540
aattattaca tgcttaacgt aattcaacag aaattatatg ataatcatcg caagaccggc    3600
aacaggattc aatcttaaga aactttattg ccaaatgttt gaacgatcgg ggatcatccg    3660
ggtctgtggc gggaactcca cgaaaatatc cgaacgcagc aagatatcgc ggtgcatctc    3720
ggtcttgcct gggcagtcgc cgccgacgcc gttgatgtgg acgccgggcc cgatcatatt    3780
gtcgctcagg atcgtggcgt tgtgcttgtc ggccgttgct gtcgtaatga tatcggcacc    3840
ttcgaccgcc tgttccgcag agatcccgtg gcgaagaac tccagcatga tccccgcg    3900 ctggaggatc atccagccgg cgtcccggaa acgattccg aagcccaacc tttcatagaa    3960
ggcggcggtg gaatcgaaat ctcgtgatgg caggttgggc gtcgcttggt cggtcatttc    4020
gaaccccaga gtcccgctca gaagaactcg tcaagaaggc gatagaaggc gatgcgctgc    4080
```

-continued

```
gaatcgggag cggcgatacc gtaaagcacg aggaagcggt cagcccattc gccgccaagc    4140
tcttcagcaa tatcacgggt agccaacgct atgtcctgat agcggtccgc cacacccagc    4200
cggccacagt cgatgaatcc agaaaagcgg ccattttcca ccatgatatt cggcaagcag    4260
gcatcgccat gggtcacgac gagatcatcg ccgtcgggca tgcgcgcctt gagcctggcg    4320
aacagttcgg ctggcgcgag ccctgatgc tcttcgtcca gatcatcctg atcgacaaga    4380
ccggcttcca tccgagtacg tgctcgctcg atgcgatgtt tcgcttggtg gtcgaatggg    4440
caggtagccg gatcaagcgt atgcagccgc cgcattgcat cagccatgat ggatactttc    4500
tcggcaggag caaggtgaga tgacaggaga tcctgccccg gcacttcgcc caatagcagc    4560
cagtcccttc ccgcttcagt gacaacgtcg agcacagctg cgcaaggaac gcccgtcgtg    4620
gccagccacg atagccgcgc tgcctcgtcc tgcagttcat tcagggcacc ggacaggtcg    4680
gtcttgacaa aaagaaccgg gcgcccctgc gctgacagcc ggaacacggc ggcatcagag    4740
cagccgattg tctgttgtgc ccagtcatag ccgaatagcc tctccaccca gcggccgga    4800
gaacctgcgt gcaatccatc ttgttcaatc atgcgaaacg atccagatcc ggtgcagatt    4860
atttggattg agagtgaata tgagactcta attggatacc gaggggaatt tatgaaacgt    4920
cagtggagca tttttgacaa gaaatatttg ctagctgata gtgaccttag gcgacttttg    4980
aacgcgcaat aatggtttct gacgtatgtg cttagctcat taaactccag aaacccgcgg    5040
ctgagtggct ccttcaacgt tgcggttctg tcagttccaa acgtaaaacg gcttgtcccg    5100
cgtcatcggc gggggtcata acgtgactcc cttaattctc cgctcatgat cagattgtcg    5160
tttcccgcct tcagtttgtg ggccatcgcc ctgatagacg gttttttcgcc ctttgacgtt    5220
ggagtccacg ttctttaata gtggactctt gttccaaact ggaacaacac tcaaccctat    5280
ctcgggctat tcttttgatt tataagggat tttgccgatt tcggaaccac catcaaacag    5340
gattttcgcc tgctggggca accagcgtg gaccgcttgc tgcaactctc tcagggccag    5400
gcggtgaagg gcaatcagct gttgcccgtc tcactggtga aaagaaaaac caccccagta    5460
cattaaaaac gtccgcaatg tgttattaag ttgtctaagc gtcaatttgt ttacaccaca    5520
atatatcctg ccaccagcca gccaacagct ccccgaccgg cagctcggca caaaatcacc    5580
actcgataca ggcagcccat cagtccggga cggcgtcagc gggagagccg ttgtaaggcg    5640
gcagactttg ctcatgttac cgatgctatt cggaagaacg gcaactaagc tgccgggttt    5700
gaaacacgga tgatctcgcg gagggtagca tgttgattgt aacgatgaca gagcgttgct    5760
gcctgtgatc aaatatcatc tccctcgcag agatccgaat tatcagcctt cttattcatt    5820
tctcgcttaa ccgtgacagg ctgtcgatct tgagaactat gccgacataa taggaaatcg    5880
ctggataaag ccgctgagga agctgagtgg cgctatttct ttagaagtga acgttgacga    5940
tatcaactcc cctatccatt gctcaccgaa tggtacaggt cggggacccg aagttccgac    6000
tgtcggcctg atgcatcccc ggctgatcga ccccagatct ggggctgaga agcccagta    6060
aggaaacaac tgtaggttcg agtcgcgaga tccccggaa ccaaggaag taggttaaac    6120
ccgctccgat caggccgagc cacgccaggc cgagaacatt ggttcctgta ggcatcggga    6180
ttggcggatc aaacactaaa gctactggaa cgagcagaag tcctccggcc gccagttgcc    6240
aggcggtaaa ggtgagcaga ggcacgggag gttgccactt gcgggtcagc acggttccga    6300
acgccatgga aaccgccccc gccaggcccg ctgcgacgcc gacaggatct agcgctgcgt    6360
ttggtgtcaa caccaacagc gccacgcccg cagttcc                           6397
```